US012379380B2

(12) United States Patent
Estandian et al.

(10) Patent No.: US 12,379,380 B2
(45) Date of Patent: Aug. 5, 2025

(54) SINGLE-MOLECULE PROTEIN AND PEPTIDE SEQUENCING

(71) Applicant: Massachusetts Institute of Technology, Cambridge, MA (US)

(72) Inventors: Daniel Masao Estandian, Cambridge, MA (US); Alexi Georges Choueiri, Chandler, AZ (US); Edward Stuart Boyden, Chestnut Hill, MA (US); Asmamaw Wassie, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/615,276

(22) Filed: Mar. 25, 2024

(65) Prior Publication Data
US 2024/0280581 A1    Aug. 22, 2024

Related U.S. Application Data

(63) Continuation of application No. 18/046,012, filed on Oct. 12, 2022, now Pat. No. 11,971,417, which is a
(Continued)

(51) Int. Cl.
*G01N 33/58* (2006.01)
*G01N 33/68* (2006.01)

(52) U.S. Cl.
CPC ......... *G01N 33/6818* (2013.01); *G01N 33/58* (2013.01); *G01N 2458/00* (2013.01)

(58) Field of Classification Search
CPC . G01N 2458/00; G01N 33/58; G01N 33/6818
See application file for complete search history.

(56) References Cited

U.S. PATENT DOCUMENTS

| 4,665,037 A | 5/1987 | Stolowitz |
| 5,254,475 A | 10/1993 | Bailey |

(Continued)

FOREIGN PATENT DOCUMENTS

| CN | 87100897 A | 2/1987 |
| JP | S62257064 A | 11/1987 |

(Continued)

OTHER PUBLICATIONS

Matsunaga et al., Boron Trifluoride-Etherate (Lewis Acid) as an Efficient Acid at Cyclization/Cleavage Reaction of D/L-Amino Acids Affording the Retention of their Original Configuration in the Edman Sequencing Method of Peptides, 1996, Biomedical Chromatography, vol. 10, pp. 95-96. (Year: 1996).*

(Continued)

*Primary Examiner* — Kathryn Elizabeth Limbaugh
(74) *Attorney, Agent, or Firm* — Pierce Atwood LLP

(57) ABSTRACT

The present description provides methods, assays and reagents useful for sequencing proteins. Sequencing proteins in a broad sense involves observing the plausible identity and order of amino acids, which is useful for sequencing single polypeptide molecules or multiple molecules of a single polypeptide. In one aspect, the methods are useful for sequencing multiple polypeptides. The methods and reagents described herein can be useful for high resolution interrogation of the proteome and enabling ultrasensitive diagnostics critical for early detection of diseases.

20 Claims, 11 Drawing Sheets

Related U.S. Application Data continuation of application No. 16/736,248, filed on Jan. 7, 2020, now Pat. No. 11,499,979.

(60) Provisional application No. 62/789,850, filed on Jan. 8, 2019.

(56) References Cited

U.S. PATENT DOCUMENTS

| | | | |
|---|---|---|---|
| 5,736,590 | A | 4/1998 | Rasmussen |
| 5,952,232 | A | 9/1999 | Rothman |
| 6,268,161 | B1 | 7/2001 | Han |
| 6,271,278 | B1 | 8/2001 | Park |
| 9,376,677 | B2 | 6/2016 | Mir |
| 9,435,810 | B2 | 9/2016 | Havranek |
| 9,566,335 | B1 | 2/2017 | Emili |
| 9,625,469 | B2 | 4/2017 | Marcotte |
| 11,214,661 | B2 | 1/2022 | Rodriques |
| 11,346,842 | B2 | 5/2022 | Boyden |
| 11,499,979 | B2 | 11/2022 | Estandian |
| 2004/0214211 | A1 | 10/2004 | Gilmanshin et al. |
| 2004/0248326 | A1 | 12/2004 | Ziaie et al. |
| 2005/0034990 | A1 | 2/2005 | Crooks et al. |
| 2005/0169962 | A1 | 8/2005 | Bhatia et al. |
| 2005/0196702 | A1 | 9/2005 | Bryant et al. |
| 2006/0110760 | A1 | 5/2006 | Kim et al. |
| 2006/0165912 | A1 | 7/2006 | Koberstein et al. |
| 2007/0023942 | A1 | 2/2007 | Andino et al. |
| 2007/0116607 | A1 | 5/2007 | Wang et al. |
| 2007/0134902 | A1 | 6/2007 | Bertino et al. |
| 2008/0286360 | A1 | 11/2008 | Shoichet et al. |
| 2009/0011141 | A1 | 1/2009 | Carter et al. |
| 2009/0096133 | A1 | 4/2009 | Doyle et al. |
| 2010/0055161 | A1 | 3/2010 | Ahn |
| 2010/0119755 | A1 | 5/2010 | Chung et al. |
| 2010/0285113 | A1 | 11/2010 | Shoichet et al. |
| 2010/0291357 | A1 | 11/2010 | Polizzotti et al. |
| 2011/0087315 | A1 | 4/2011 | Richardson-Burns et al. |
| 2011/0091717 | A1 | 4/2011 | Weiss |
| 2012/0029416 | A1 | 2/2012 | Parker et al. |
| 2012/0310223 | A1 | 12/2012 | Knox et al. |
| 2014/0087139 | A1 | 3/2014 | Rowley et al. |
| 2014/0193651 | A1 | 7/2014 | Kharlampieva et al. |
| 2014/0204364 | A1 | 7/2014 | Asher et al. |
| 2014/0273004 | A1 | 9/2014 | Havranek et al. |
| 2015/0240035 | A1 | 8/2015 | Lewicki et al. |
| 2017/0002053 | A1 | 1/2017 | Julius et al. |
| 2017/0067096 | A1 | 3/2017 | Wassie et al. |
| 2018/0299460 | A1 | 10/2018 | Emili |
| 2018/0372752 | A1 | 12/2018 | Emili et al. |
| 2019/0194709 | A1 | 6/2019 | Church et al. |
| 2020/0209249 | A1 | 7/2020 | Reed et al. |
| 2022/0112553 | A1 | 4/2022 | Boyden |
| 2022/0291226 | A1 | 9/2022 | Boyden |

FOREIGN PATENT DOCUMENTS

| | | |
|---|---|---|
| WO | 2010065531 A1 | 6/2010 |
| WO | 2014152984 A1 | 9/2014 |
| WO | 2017192633 A1 | 11/2017 |

OTHER PUBLICATIONS

Bellin, DL, et al. "Interfacing CMOS Electronics to Biological Systems: from Single Molecules to Cellular Communities Biomedical Circuits and Systems Conference" (BioCAS), 2014 IEEE; 2014. p. 476-479.
Bentley, et al. "Accurate whole human genome sequencing using reversible terminator chemistry" Nature vol. 456, Nov. 6, 2008, p. 53-59.
Borgo, B "Strategies for Computational Protein Design with Application to the Development of a Biomolecular Tool-kit for Single Molecule Protein Sequencing" Theses and Dissertations (ETDs) al//openscholarshipwustledu/eld/1221 May 2014.
Borgo, B., et al. "Motif-directed redesign of enzyme specificity" Protein Science 2014; vol. 23, p. 312-320.
Borgo, et al. "Computer-aided design of a catalyst for Edman degradation utilizing substrate-assisted catalysis" Protein Science, Dec. 16, 2014 doi: 101002/pro2633, vol. 24, p. 571-579.
Brenner, et al. "Gene expression analysis by massively parallel signature sequencing (MPSS) on microbead arrays" Nature Biotechnology vol. 18, p. 630-634 (2000).
Chandradoss SD et al. "Surface Passivation for Single-molecule Protein Studies" Journal of Visualized Experiments: JoVE Apr. 2014; (86).
Chaudhuri, R.G., et al., "Core/Shell Nanoparticles: Classes, Properties, Synthesis" Chem. Rev. 2012, 112, 4, 2373-2433.
Cui Y, et al. "Nanowire Nanosensors for Highly Sensitive and Selective Detection of Biological and Chemical Species" Science 2001;293(5533): 1289-1292.
Cutler, J., et al., "Spherical Nucleic Acids," Journal of the American Chemical Society, vol. 134, pp. 1376-1391 (2012).
Dempsey, GT, et al. "Evaluation of fluorophores for optimal performance in localization-based super-resolution imaging" Nature Methods 2011;8(12): 1027-1036.
Edman, P, "Method for Determination of the Amino Acid Sequence in Peptides" Acta Chem Scand. (1950) 4(7):283-293.
Extended European Search Report issued Sep. 13, 2022, in European Patent Application No. 20739125.1 (8 pages).
Finkelstein, et al. "Supported Lipid Bilayers and DNA Curtains for High-Throughput Single-Molecule Studies" Methods Mol Biol 2011 ; 745: 447-461.
Foote, J et al. "Kinetic and affinity limits on antibodies produced during immune responses" PNAS (USA) vol. 92, pp. 1254-1256, Feb. 1995.
Grammel, et al., "Chemical reporters for biological discovery" Nature Chemical Biology, vol. 9, published online Jul. 18, 2013, pp. 475-484.
Groll, J, et al. "Chapter 1—Star Polymer Surface Passivation for Single-Molecule Detection" Methods in Enzymology vol. 472 Elsevier; 2010 p. 1-18.
Guo, N, et al. "CMOS Time-Resolved, Contact, and Multispectral Fluorescence Imaging for DNA Molecular Diagnostics" Sensors 2014; 14(11 ):20602-20619.
International Search Report and Written Opinion from the International Searching Authority dated Apr. 2, 2020 from corresponding International Patent Application N. PCT/US20/12502 filed on Jan. 7, 2020.
Joo C, et al "Bringing single-molecule spectroscopy to macromolecular protein complexes" Trends Biochem Sci Jan. 2013 ; 38(1): 30-37.
Joo et al. "Single-Molecule FRET with Total Internal Reflection Microscopy" Health Sciences (2012) 1223-1237.
Jungmann, R, et al. "Single-Molecule Kinetics and Super-Resolution Microscopy by Fluorescence Imaging of Transient Binding on DNA Origami" Nano letters 2010; 10(11 ):4756-4761.
Kim, A, et al. "Ultrasensitive, label-free, and real-time immunodetection using silicon field-effect transistors" Applied Physics Letters 91, 103901 (2007).
Laursen, R.A "Solid-Phase Edman Degradation—An Automatic Peptide Sequencer" Eur J. Biochem 20 (1971) p. 9-102.
Li et al. "Design and Synthesis of Minimalist Terminal Alkyne-Containing Diazirine Photo-Crosslinkers and Their incorporation into Kinase Inhibitors for Cell- and Tissue-Based Proteome Profiling," Angew. Chem., 2013, p. 6713-8718, DOI: 10.1002/ange. 201300683.
Lu, N. et al. "Label-Free and Rapid Electrical Detection of hTSH with CMOS-Compatible Silicon Nanowire Transistor Arrays" ACS Applied Materials & Interfaces 2014; 6(22) p. 20378-20384.
Mitra, et al. "Fluorescent in situ sequencing on polymerase colonies", Analytical Biochem 2003;320, p. 55-65.
Nemoto, N. et al. "Fluorescence labeling of the C-terminus of proteins with a puromycin analogue in cell-free translation systems" FEBS letters 1999; 462(1) p. 43-46.
Pan, H, et al. "A simple procedure to improve the surface passivation for single molecule fluorescence studies" Physical Biology 2015; 12(4):045006.

(56) References Cited

OTHER PUBLICATIONS

Rothberg, JM, et al. "An integrated semiconductor device enabling non-optical genome sequencing" Nature J011; 475(7356) p. 348-352.
Sharonov, A. et al. "Wide-field subdiffraction imaging by accumulated binding of diffusing probes" PNAS Dec. 12, 2006, vol. 103, No. 50, p. 18911-18916.
Shendure J et al. "Advanced Sequencing Technologies: Methods and Goals" Nature Reviews Genetics 2004; 5(5) p. 335-344.
Shendure, et al. "The expanding scope of DNA sequencing" Nat Biotechnol Nov. 2012; 30(11) p. 1084-1094.
Sorgenfrei, S, et al. "Label-free field-effect-based single-molecule detection of DNA hybridization kinetics" Nat Nanotechnol Feb. 2011; 6(2): p. 126-132.
Swaminathan, et al. "A theoretical justification for single molecule peptide sequencing" bioRxiv preprint doi: https://doi.org/101101/010587.
Tessler, et al. "Nanogel surface coatings for improved single-molecule imaging substrates" Journal of the Royal Society Interface 2011; 8 p. 1400-1408.
Tessler, L. et al. "Sensitive single-molecule protein quantification and protein complex detection in a microarray format" Proteomics 2011; 11(24) p. 4731-4735.
Ting, L., "Preparation of novel core-shell nanoparticles by electrochemical synthesis," Trans. Nonferrous Met. Soc. China, vol. 17, pp. 1343-1346 (2007).
Van Ginkel, et al. "Single-Molecule Peptide Fingerprinting" Biophysical Journal 2017; 112(3):471a.
Van Oijen "Single-molecule approaches to characterizing kinetics of biomolecular interactions" AM Current Opinion in Biotechnology, 2011 ;22(1) p. 75-80.
Xu, G, et al. "Chemoenzymatic labeling of protein C-termini for positive selection of C-terminal peptides" ACS Chemical Biology 2011; 6(10) p. 1015-1020.
Yao, et al. "Single-molecule protein sequencing through fingerprinting: computational assessment" Physical Biology 2015; 12(5):055003.
U.S. Appl. No. 18/415,295, filed Jan. 17, 2024.
Neely, R.K. et al., "Optical mapping of DNA: Single-molecule-based methods for mapping genomes." Biopolymers 95.5 (2011): 298-311.
Gao, R, et al. "Q&A: expansion microscopy." BMC biology 15 (2017): 1-9.
Kubalova et al. Prospects and limitations of expansion microscopy in chromatin ultrastructure determination. Chromosome Res. Dec. 2020;28(3-4):355-368. doi: 10.1007/s10577-020-09637-y. Epub Sep. 17, 2020. PM ID: 32939606; PMCID: PMC7691311 (Year: 2020).
Yuan et al., Advances in optical mapping for genomic research. Com put Struct Biotechnol J. Aug. 1, 2020 ; 18:2051-2062. doi: 10.1016/j.csbj.2020.07.018. PMID: 32802277; PMCID: PMC7419273; (Year: 2020).

\* cited by examiner

N-terminal conjugation efficiency

N-terminal conjugation efficiency time course

N-terminal cleavage efficiency

Antibody binding – Varying the adjacent amino acid to tryptophan

Fig. 6A

N-Terminal cleavage with ClickP or PITC attached

REACTION 3

SINGLE-MOLECULE PROTEIN AND PEPTIDE SEQUENCING

RELATED APPLICATION

This application is a continuation of, and claims the benefit of, U.S. Nonprovisional application Ser. No. 18/046,012, filed on Oct. 12, 2022, which claims priority to U.S. Nonprovisional application Ser. No. 16/736,248, filed on Jan. 7, 2020, which claims priority to U.S. Provisional Application No. 62/789,850, filed on Jan. 8, 2019. The entire teachings of the above applications are incorporated herein by reference.

BACKGROUND

Proteins serve critical structural and dynamic functional roles at the cellular level of all living organisms. Understanding protein contribution to biological function is critical and rests on having appropriate technologies for quantification and identification. The central dogma of molecular biology, information flow from DNA to RNA to protein, has been studied for decades as these molecules are critical to cell function and diversity. The advent of polymerase chain reaction (PCR) amplification of nucleic acid was pivotal in advancing the high-throughput molecular interrogation and analysis of DNA and RNA at the whole-genome and transcriptome level. In contrast, studying proteins has lagged technologically since there is no equivalent of PCR to amplify and detect low-copy number proteins. Instead, protein sequencing and identification methods have relied on ensemble measurements from many cells which masks cell-to-cell variations. While some researchers have turned to transcriptomics as a proxy to the protein composition within cells, it is critical to note that gene expression at the transcriptomic level weakly correlates with the proteomic profile due to variability in translational efficiency of different mRNAs, and the difference between mRNA and protein lifetimes. In addition, post-translational modifications also result in significant variability of protein abundance and their primary sequence with respect to the transcriptome. Vital biological processes such as synaptic plasticity, metabolic signaling pathways and stem cell differentiation, all depend on protein expression. Many diseases also originate from genetic mutations that are in turn translated to a single or set of aberrant proteins. Diseases such as cancer and neurodegeneration tend to have triggered mutations of unclear origins and polygenic interactions. They can be best understood and addressed at the proteomic level, since their pathology is directly related to disrupted proteostasis at the cellular level.

Advancements in proteomics have lagged behind while DNA sequencing has rapidly advanced the study of genomics primarily due to technologies that allow for high-throughput sequencing. Current methodologies for studying proteins include Mass Spectrometry, Edman sequencing and Immunohistochemistry (IHC).

Mass spectrometry enables protein identification and quantification based on the mass/charge ratio of peptide fragments, which can be bioinformatically mapped back to a genomic database. While this technique has made significant advancements, it has yet to quantify a complete set of proteins from a biological system. The technology exhibits attomole detection sensitivities for whole proteins and sub-attomole sensitivities after fractionation. The sensitivity of mass spectrometry is limiting since low copy-number proteins that make up about 10% of mammalian protein expression remain undetected and are functionally important despite low abundance.

The other method used for protein sequencing is the Edman degradation reaction. Edman degradation allows for sequential and selective removal of single N-terminal amino acids, subsequently identified via HPLC, High-Performance Liquid Chromatography. Edman protein sequencing is a proven method to selectively remove the first N-terminal amino acid for identification in which phenyl isothiocyanate (PITC) is used to conjugate to the N-terminal amino acid, then upon acid and heat treatment, the PITC-labeled N-terminal amino acid is removed. Although Edman sequencing can have 98% efficiency, a major drawback is that it is inherently low throughput, requiring a single highly purified protein and not applicable to systems-wide biology. Both Edman degradation and mass spectrometry can sequence proteins but lack single molecule sensitivity and do not provide spatial information of proteins in the context of cells.

In regards to spatial information, immunohistochemistry is a protein identification method that allows us to visualize cellular localization of proteins but does not provide sequence information. Immunohistochemistry involves the identification of proteins via recognition with fluorophore-conjugated antibodies. This approach excludes protein sequence information but can identify proteins and their respective localizations. A major limitation is the scalability, since even the perfect construction of specific antibodies for every protein in the proteome would require around 25,000 antibodies and, ~6250 rounds of four-color imaging. Any 1-to-1 protein tagging scheme will likely fail to scale to the entire proteome.

A major obstacle in protein sequencing is the lack of natural enzymes and biomolecules that probe amino acids on a peptide. For example, there does not exist protein amplification processes analogous to PCR for nucleic acid, so the approach to sequencing via single-molecule strategies is appropriate, requiring the detection of individual amino acids.

Current proposed approaches to single molecule protein sequencing rely either on fluorescent read-out via covalent chemical modifications of peptide or protein residues, probing with N-terminal-specific amino-acid binders (NAABs), or translocating peptides through a nanopore with a voltage applied across the membrane. Chemical modifications of amino acids on the internal peptide chain may be vulnerable to low efficiencies due to steric hindrance caused by adjacent chemical labels, and there is also a limited number of available reactive amino acids and chemistries for labeling of all 20 amino acids. A major issue using nanopores for protein sequencing can be attributed to the non-uniform charge distribution of amino acid residues and the analytical challenge of deconvolving electric recordings to discriminate between amino acids.

In the case of N-terminal amino-acid binders, peptides are immobilized to substrates by the C-terminus so the N-terminus is accessible to binders and sequential Edman degradation. Engineering highly specific, strong N-terminal binders that are not affected by the presence of variable neighboring amino acids found across different peptides is challenging. Neighboring amino acids may affect N-terminal binding by introducing variation in charge, sterics and secondary structure. This can be referred to as the "local environment" problem. For example, when attempting to recognize the N-terminal amino acid of a peptide, the combinations of varying amino acids on the rest of the peptide results in many possible sequences that impose inconsistent interactions with an N-terminal binder.

The lack of technology for high-resolution protein-level analyses represents a significant gap in advancing important biological research.

SUMMARY OF THE INVENTION

The invention provides a method for identifying the terminal amino acid of a peptide. In embodiments, the method comprises contacting the peptide with a ClickP compound, wherein the ClickP compound binds to a terminal amino acid or a terminal amino acid derivative of the peptide to form a ClickP-peptide complex, tethering the ClickP-peptide complex to a substrate; cleaving the complex from the peptide thereby providing a ClickP-amino acid complex bound to the substrate; and detecting the ClickP-amino acid complex.

The invention also provides a method for identifying the terminal amino acid of two or more peptides in a sample. In embodiments, the method comprises independently affixing the two or more peptides to an attachment point on a substrate; contacting the peptides with ClickP compounds, wherein the ClickP compounds bind to a terminal amino acid or terminal amino acid derivative to form a ClickP-pepetide complex, tethering the ClickP-peptide complexes to the substrate; cleaving the ClickP-peptide complexes from the peptide thereby providing a ClickP-amino acid complex bound to the substrate; and detecting the ClickP-amino acid complexes.

The invention also provides a method for sequencing of at least a portion of a peptide. In embodiments, the method comprises contacting the peptide with a ClickP compound, wherein the ClickP compound binds to a terminal amino acid or terminal amino acid derivative of the peptide to form a ClickP-peptide complex, tethering the ClickP-peptide complex to a substrate; cleaving the ClickP-peptide complex from the peptide to form a ClickP-amino acid complex; detecting the ClickP-amino acid complex; identifying the amino acid of the ClickP-amino acid complex; releasing the ClickP-amino acid complex from the substrate; and repeating these steps.

The invention also provides a method for sequencing at least a portion of two or more peptides in a sample independently affixed attachment points on a substrate. In embodiments, the method comprises contacting the two or more peptides with a ClickP compounds, wherein the ClickP compounds bind to a terminal amino acid or terminal amino acid derivative to form a ClickP-peptide complexes, tethering the ClickP-peptide complexes to the substrate; cleaving the ClickP-peptide complexes from the peptide to form ClickP-amino acid complexes; detecting the ClickP-amino acid complexes; identifying the amino acid of the ClickP-amino acid complexes; releasing the ClickP-amino acid complexes from the substrate; and repeating these steps.

The invention also provides a ClickP-amino acid complex. In embodiments, the ClickP-amino acid complex comprises a ClickP compound bound to one of 20 natural proteinogenic amino acids; a ClickP compound bound to a post-translationally modified amino acid; or a ClickP compound bound to a derivative of (a) or (b).

The invention also provides a ClickP-amino acid complex binder. In embodiments, the ClickP-amino acid complex binder comprises a binder that binds to a subgroup of the 20 natural proteinogenic amino acids complexed with ClickP; a binder that binds to a subgroup of post-translationally modified amino acids complexed with ClickP; or a binder that binds to a derivative of (a) or (b).

In embodiments, the ClickP-amino acid complex binder comprises a binder that binds to one of 20 natural proteinogenic amino acids complexed with ClickP; a binder that binds to a post-translationally modified amino acids complexed with ClickP; or a binder that binds to a derivative of (a) or (b).

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3A depicts N-terminal conjugation efficiency. FIG. 3B depicts N-terminal conjugation efficiency time course. FIG. 3C depicts N-terminal cleavage efficiency.

FIG. 6A and FIG. 6B depict the local environment problem of a tryptophan targeting antibody and its ability to selectively target ClickP-tryptophan over other ClickP-amino acid complexes.

DETAILED DESCRIPTION

Figure 1:
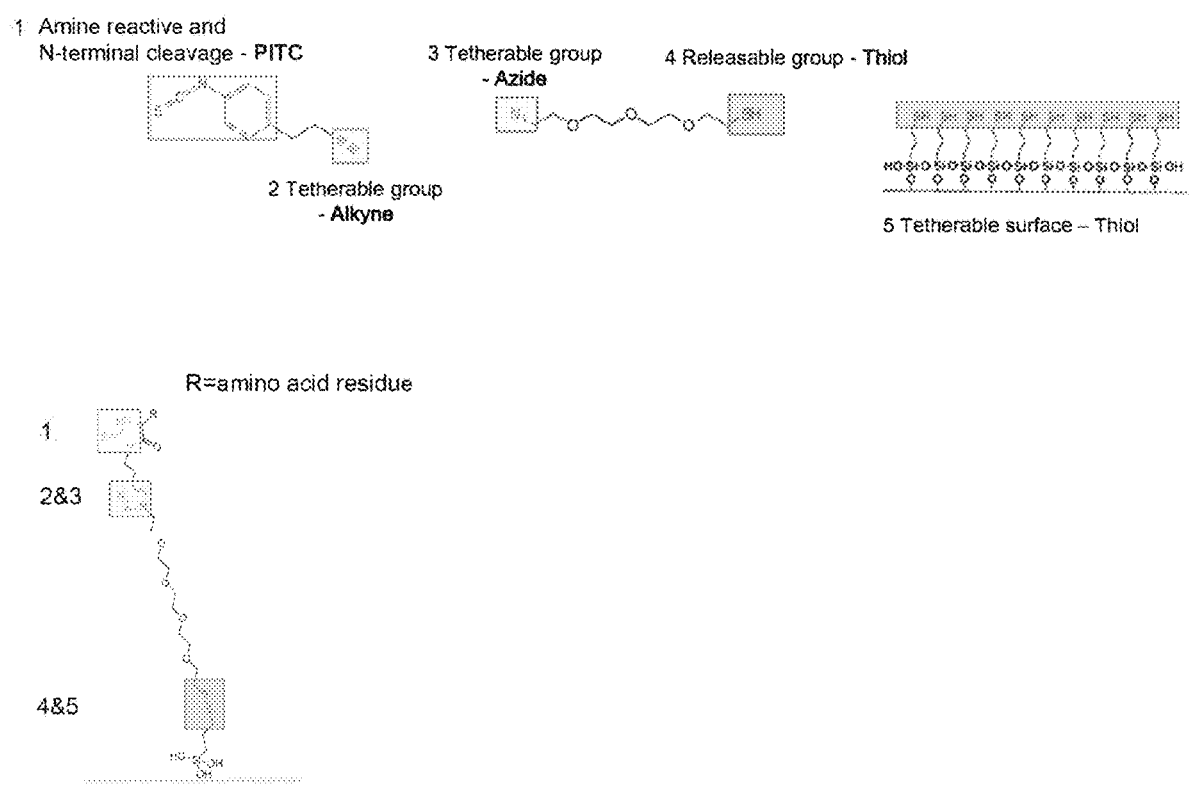
FIG. 1 depicts one example of a ClickP compound of Formula I comprising PITC as the primary amine reactive and cleavage group and an alkyne as the tethering group, an azide-thiol linker, a thiol-functionalized surface.
Figure 2:
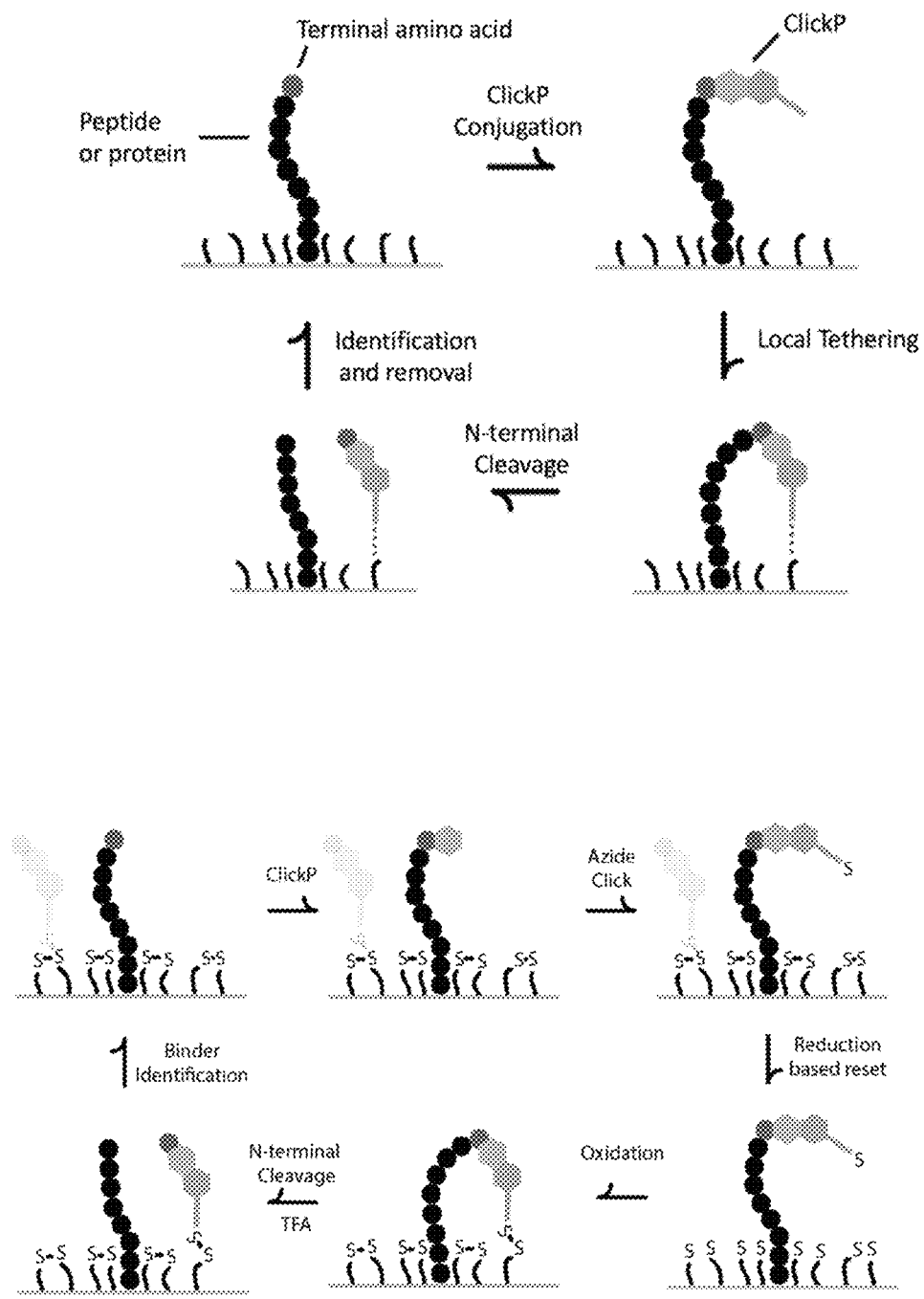
FIG. 2 depicts a workflow for single molecule peptide sequencing and N-terminal amino acid identification using ClickP.

The present description provides methods, assays and reagents useful for sequencing proteins. Sequencing proteins in a broad sense involves observing the plausible identity and order of amino acids.

In one aspect, the methods are useful for sequencing single polypeptide molecules or multiple molecules of a single polypeptide. In one aspect, the methods are useful for sequencing multiple polypeptides.

In one aspect, the methods and reagents are useful for determining the N-terminal amino acid of a polypeptide. In one aspect, the methods are useful for the simultaneous sequencing of a plurality of single polypeptide molecules, such as for the basis of massively parallel sequencing techniques. Accordingly, samples comprising a mixture of different proteins can be assayed according to the methods described herein to generate sequence information regarding individual protein molecules in the sample. In a further aspect, the methods are useful for protein expression profiling in complex samples. For example, the methods are useful for generating both quantitative (frequency) and qualitative (sequence) data for proteins contained in a sample.

In one embodiment, the invention allows for single-molecule identification and sequencing of proteins. The methods and reagents described herein can be useful for high resolution interrogation of the proteome and enabling ultrasensitive diagnostics critical for early detection of diseases.

In one aspect, the invention provides compounds, compositions, and methods for identifying the terminal amino acid of a peptide. In one embodiment, the invention provides reagents for N-terminal amino acid isolation and identification, such as an N-terminal amino acid isolation reagent and N-terminal amino acid isolation reagent-amino acid complex binders. In one embodiment, the invention provides reagents for C-terminal amino acid isolation and identification, such as a C-terminal amino acid isolation reagent and C-terminal amino acid isolation reagent-amino acid complex binders. In one embodiment, a N-terminal amino acid is identified. In one embodiment, a C-terminal amino acid is identified.

The N-terminal or C-terminal amino acid isolation reagents are also referred to herein as "ClickP". In one embodiment, the ClickP compound has the structure of Formula I:

Formula I wherein
A is a terminal amino acid reactive and cleaving group;
B is a releasable group;
C is a tetherable group; and
L1 and L2 are independent spacers.

The terminal amino acid reactive group reacts to and binds the terminal amino acid of a peptide. When used for N-terminal amino acid isolation the terminal amino acid reactive group of the ClickP compound comprises a primary amine reactive group that conjugates to the free amine at the N-terminal end of the peptide to form a ClickP-peptide complex.

When used for C-terminal amino acid isolation the terminal amino acid reactive group of the ClickP compound comprises a C-terminal reactive group that conjugates to the modified or unmodified carboxylic group at the C-terminal end of the peptide to form a ClickP-peptide complex.

In embodiments, the terminal amino acid reactive group is a primary amine reactive group. In one embodiment, the primary amine reactive group includes, but not limited to, isothiocyanate, phenyl isothiocyanate (PITC), isocyanates, acyl azides, N-hydroxysuccinimide esters (NHS esters), sulfonyl chlorides, aldehydes, glyoxals, epoxides, oxiranes, carbonates, aryl halides, imidoesters, carbodiimides, anhydrides, and fluorophenyl esters. In one embodiment, the reagent is phenyl isothiocyanate (PITC).

In certain embodiments, the N-terminal amino acid, or derivative thereof, and the ClickP compound can be contacted under conditions that allow the N-terminal amino acid to conjugate to the primary amine reactive group of the ClickP to form a complex.

In one embodiment, the terminal amino acid reactive group is a C-terminal reactive group. In one embodiment, the C-terminal reactive group includes, but is not limited to, isothiocyanate, tetrabutylammonium isothiocyanate, diphenylphosphoryl isothiocyanate, acetyl chloride, cyanogen bromide, isothiocyanate, sodium thiocyanate, ammonium thiocyanate, and carboxypeptidases.

In certain embodiments, the C-terminal amino acid, or derivative thereof, and the ClickP compound can be contacted under conditions that allow the modified or unmodified C-terminal amino acid to conjugate to C-terminal reactive group of the ClickP, to form a complex.

In some embodiments, the cleaving group is the same as the terminal amino acid reactive group. In one embodiment, the N-terminal cleaving group is involved in the chemical removal of the terminal amino acid from the peptide. In one embodiment, the N-terminal cleaving group is involved in the chemical removal of the terminal amino acid from the peptide to forms the ClickP-amino acid complex. In one embodiment, the cleaving group is PITC or isothiocyanate. In one embodiment, the cleaving group is assisted by engineered or wildtype enzymes such as peptidases or proteases.

In one embodiment, the ClickP amino acid complex is the ClickP compound conjugated to the amino acid following cleavage from the peptide. In one embodiment, the ClickP amino acid complex can be chemically derivatized to be antigenic. In one embodiment the ClickP-amino acid complex can be, but is not limited to, the following derivatized forms: thiazolone, thiohydantoin, or thiocarbamyl.

In some embodiments, the functions of reacting to amines and cleaving the terminal amino acid from the peptide can be performed by the primary amine reactive group. In some embodiments, the primary amine reactive group having both of these functions includes, but is not limited to, isothiocyanate, phenyl isothiocyanate (PITC). In one embodiment, the primary amine reactive group is phenyl isothiocyanate (PITC). In one embodiment, the primary amine reactive group is isothiocyanate.

In some embodiments, the functions of reacting to the C-terminus and cleaving amino acids can be performed by the same chemical group. In one embodiment, the C-terminal cleaving group is involved in the chemical removal of the terminal amino acid from the peptide to forms the ClickP-amino acid complex. In one embodiment, the cleaving group is isothiocyanate, tetrabutylammonium isothiocyanate, or diphenylphosphoryl isothiocyanate.

In one embodiment, the tethering group includes, but is not limited to, isothiocyanate, tetrabutylammonium isothiocyanate, diphenylphosphoryl isothiocyanate, azide, alkyne, Dibenzocyclooctyne (DBCO), maleimide, succinimide, thiol-thiol disulfide bonds, Tetrazine, TCO, Vinyl, methylcyclopropene, a primary amine, a carboxylic acid an alkyne, acryloyl, allyl, and an aldehyde.

The tethering group can conjugate to a functionalized substrate such as a functionalized glass surface or integrated into a polymer network under conditions that allows for conjugation, thereby immobilizing the ClickP-peptide complex on the substrate.

In embodiments, the releasable group is involved in the removal of part or all of the ClickP-amino acid complex. In some embodiments, the ClickP-amino acid complex can be released from the substrate under certain substrate release conditions which are not the binding conditions or the amino acid release conditions. In some embodiements, the releasable group can be but is not limited to a disulfide, peptide, oligonucleotide, or carbohydrate.

The term "substrate release conditions" refers to release conditions in which a ClickP-amino acid complex will be released from a substrate. The substrate release conditions can include, but are not limited to, acidic conditions, basic conditions, presence of a nucleophile, presence of a Lewis base, presence of a non-nucleophilic base, presence of a nucleophilic base, presence of a thiol, oxidation conditions, reduction conditions, presence of a catalyst, presence of an engineered or wildtype enzyme, exposure to visible light, exposure to ultraviolet light, or combinations thereof. Release conditions can include, but not limited to, aqueous solvents (such as water), organic solvents (such as dioaxane, DMSO, THF, DMF, Toluene, acetonitrile), or combinations thereof. In certain embodiments, acidic conditions can include the use of hydrofluoric acid (HF), or hydrochloric acid (HCl). In certain embodiments, basic conditions can include the use of pyridine, ammonia, piperidine, 4-dimethylaminopyridine (DMAP), N,N-diisopropylethylamine (DIEA), piperizine, morpholine, dicyclohexylamine, triethylamine, or diethylamine.

By way of explanation, and not intended to limit the invention, the "cleaving" group of the ClickP compound acts to remove the terminal amino acid from the peptide while the "releasable" group provides a mechanism to release the ClickP-amino acid complex from the substrate. Removing the ClickP-amino acid complex from the substrate allows for the identification of sequential amino acids.

In some embodiments, a spacer is used to provide sufficient steric separation between the functional groups of the ClickP compound to avoid interference with reaction kinetics. In some embodiments the spacer includes, but is not limited to, polymers and biopolymers such as polyethylene glycol (PEG) chains, Aminohexanoic acid (Ahx), 12-aminododecanoic acid, O2Oc, O1Pen-O1Pen, Ttds, Beta-Alanine, hydrocarbon chains, amino acids, peptides, peptide bonds, and nucleic acid.

In one embodiment, the ClickP compound can comprise a releasable group before the tethering group.

In one embodiment, the ClickP compound can comprise a releasable group after the tethering group.

In one embodiment, the ClickP compound can comprise a releasable group that is reversible with the ability to both tether and be cleaved dependent on the condition.

Example of a releasable group with tethering group include but are not limited to:
spacer-alkyne-azide-spacer-thiol-thiol-substrate;
spacer-thiol-thiol-spacer-alkyne-azide-substrate; and
spacer-thiol-thiol-substrate;
wherein the underlined portion is the functionalized substrate tethering the ClickP tethering group. The thiol-thiol group is a releasable group that releases the part of or the whole ClickP complex under certain conditions from the substrate. The releasable group can be before or after the tethering group. In the case of thiol, it can act as both the tethering group and the releasable group.

The ClickP compound comprises a reactive group that conjugates to the terminal amino acid of the peptide; a tethering group that immobilizes the ClickP-peptide complex to a physical substrate; and a cleaving group that allows for the removal of the ClickP compound and the bound terminal amino acid from the peptide resulting in a ClickP-amino acid complex; and a releasable group that allows for the release of the complex from the physical substrate.

In one embodiment ClickP compound conjugates to the terminal amino acid of the peptide to form the ClickP-peptide complex. The ClickP-peptide complex is then locally tethered to a physical substrate. The ClickP-peptide complex is subsequently cleaved from the peptide resulting in a ClickP-amino acid complex. After detection and/or identification of the amino acid of the ClickP-amino acid complex, the ClickP-amino acid complex can optionally be released from the substrate to allow for following consecutive rounds of sequencing. In some embodiments, the tethering group is that same as the releasable group.

In some embodiments, the ClickP-amino acid complex is antigenic. In some embodiments, a portion of the ClickP-amino acid complex is antigenic. The antigenic portion will include the attached amino acid and the following portions from Formula I—only A, A and B, A and C, or A B and C. In embodiments, the antigenic portion will include the attached amino acid and A from Formula I. In embodiments, the antigenic portion will include the attached amino acid and A and B from Formula I. In embodiments, the antigenic portion will include the attached amino acid and A and C from Formula I. In embodiments, the antigenic portion will include the attached amino acid and A, B, and C from Formula I.

In one embodiment, Formula II depicts a portion of ClickP such that the releasable functional group can be attached later to provide flexibility to test various releasable linkers.

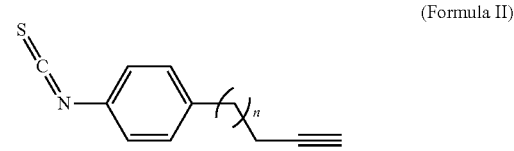

(Formula II)

wherein n is is any number from 0 to 500. In one embodiment, n is any number from 0 to 250. In one embodiment, n is any number from 0 to 100. In one embodiment, n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In one embodiment, n is 0, 1, 2, 3, 4, 5, 6, 7, 8, 9, 10, 11, 12, 13, 14, 15, 16, 17, 18, 19, 20, 21, 22, 23, 24, or 25. In one embodiment, n is 0, 1, 2, 3, 4, 5, 6, 7, 8, 9, or 10. In one embodiment, n is 1, 2, 3, 4, or 5. In one embodiment, n is 1.

In one embodiment, the ClickP compound can tether directly to a functionalized surface of a substrate. For example, if the functionalize surface is an azide containing surface, then a ClickP compound comprising a group that conjugates to azides, e.g., alkynes, can tether directly to the surface. The conditional copper-catalyzed (Cu+) click chemistry of alkyne-azide bonds is bioorthgonal with a high yield and high reaction specificity suitable for isolating target molecule in complex biological environments.

The contacting and binding of components in a ClickP complex, or a ClickP complex-substrate complex can occur in a solvent including, but not limited to, aqueous solvents (such as water) or organic solvents (such as dioaxane, DMSO, THF, DMF, Toluene, acetonitrile).

FIG. 1 shows one example of a ClickP compound of Formula I comprising PITC as the terminal amine reactive and cleaving group and an alkyne as the tethering group, an azide-thiol linker, and a thiol-functionalized surface. As shown in FIG. 1, PITC can bind to the terminal amino acid of a peptide to form a ClickP-peptide complex. The alkyne group conjugates to the azide tetherable group of the azide-thiol linker, which forms a disulfide bond with a thiol-functionalized surface. The alkyne group on ClickP allows for the addition of any modular azide linker such as, but not limited to, an azide-thiol, to form bonds to various types of functionalized surfaces. The disulfide bond allows ClickP to be released from surfaces with a reducing agent such as tris(2-carboxyethyl)phosphine (TCEP) that cleaves disulfide bonds. A releasable group for the removal of ClickP-bound amino acid from the surface allows for the isolation and identification of the next, terminal, amino acid on a peptide.

In one embodiment, the invention provides a method for isolating amino acids using compounds to tether the terminal amino acid of the peptide to a physical substrate and to cleave the terminal amino acid to then be identified free from the peptide. The isolation of the terminal amino acid from the peptide allows for more selective and/or higher affinity binding of amino acids that is not influenced by the rest of the peptide.

In one embodiment, identifying the terminal amino acid of a peptide comprises contacting the peptide with a ClickP compound, wherein the ClickP compound binds to a terminal amino acid or a terminal amino acid derivative of the peptide to form a ClickP-peptide complex The ClickP-peptide complex is tethered to a substrate. After tethering, the ClickP-peptide complex is cleaved from the peptide to form the ClickP-amino acid complex. The ClickP-amino acid complex can then be used for the detection and/or identification of the amino acid of the ClickP-amino acid complex.

In one embodiment, the invention provides a method for the isolation and identification of N-terminal amino acids, or derivatives thereof, of a polypeptide or protein. Isolation of N-terminal amino acids with ClickP will involve conjugation of the ClickP compound to the N-terminal amino acid of a polypeptide or a derivative thereof, to form a ClickP-peptide complex; conditional tethering of the ClickP-peptide complex to a substrate, cleavage of the ClickP-peptide complex from the peptide forming the ClickP-amino acid complex; and detection and/or identification of the ClickP-amino acid complex.

In one embodiment, the invention provides a method for the isolation and identification of C-terminal amino acids, or derivatives thereof, of a peptide. Isolation of C-terminal amino acids with ClickP will involve conjugation of the ClickP compound to the C-terminal amino acid of a peptide or a derivative thereof, to form a ClickP-peptide complex; conditional tethering of the ClickP-peptide complex to a substrate, cleavage of the ClickP-peptide complex from the peptide, to form a ClickP-amino acid complex; and detection and/or identification of the ClickP-amino acid complex.

In one embodiment, there is provided a method for identifying the terminal amino acid of a plurality of peptides in a sample.

In one embodiment, the method comprises affixing the plurality of peptides in the sample to a plurality of attachment points on a functionalized substrate; contacting the peptides with a plurality of ClickP compounds, wherein the ClickP compounds bind to a terminal amino acid or N-terminal amino acid derivative to form a ClickP-peptide complexes, tethering the ClickP-peptide complexes to the substrate; cleaving the ClickP-peptide complexes from the peptide to form ClickP-amino acid complexes; and detecting and/or identifying the amino acids of the ClickP-amino acid complexes.

In embodiments of the methods disclosed herein, the methods optionally comprise washing away excess and/or unbound ClickP compound prior to the step of cleaving the ClickP-peptide complex from the polypeptide or protein.

Sequencing of peptides with ClickP will involve conjugation of the ClickP compound to the terminal amino acid of a peptide or a derivative of a terminal amino acid of a peptide to form a ClickP-peptide complex; conditional tethering of the ClickP-peptide complex to a substrate, cleavage of the ClickP-peptide from the peptide to form a ClickP-amino acid complex; detection and identification of the ClickP-amino acid complex; and release of the immobilized ClickP-amino acid complex from the substrate for the next cycle.

In one embodiment, detecting and/or identifying the amino acid of the ClickP-amino acid complex comprises contacting the ClickP-amino acid complex with a ClickP-amino acid complex binder, wherein the ClickP-amino acid complex binder binds to a ClickP-amino acid complex or a subgroup of ClickP-amino acid complexes; and detecting the ClickP-amino acid complex binder bound to the ClickP-amino acid complex. Detecting binding of the binder to the ClickP-amino acid complex allows for the identification of the terminal amino acid of the peptide.

In one embodiment, detecting and/or identifying the amino acid of the ClickP-amino acid complex comprises contacting the ClickP-amino acid complex with a plurality of ClickP-amino acid complex binders, wherein each ClickP-amino acid complex binder preferentially binds to a specific ClickP-amino acid complex or a subgroup of ClickP-amino acid complexes; and detecting the ClickP-amino acid complex binder bound to the ClickP-amino acid complex. By detecting the ClickP-amino acid complex binder bound to the ClickP-amino acid complex allows for identifying the terminal amino acid or subgroup of amino acids of the peptide.

It has been determined that ClickP and ClickP-amino acid complex binders can be used to generate sequence information by identifying the terminal amino acids of a peptide. The inventors have also determined that by first affixing the peptide molecule to a substrate, it is possible to determine the sequence of that immobilized peptide by iteratively detecting the ClickP-amino acid complex at that same location on the substrate.

In one embodiment, detecting and/or identifying the amino acid of the ClickP-amino acid complex can comprise direct detection through wavelengths of light. In one embodiment, ramam spectrum from single ClickP-amino acid complexes are detected to identify the complex. In one embodiment, surface enhanced Raman spectroscopy is used to detect and/or identify the ClickP-amino acid complex. In one embodiment, the Raman spectrum for each ClickP-amino acid complex is distinguishable from one another. In one embodiment, the Raman spectrum for each ClickP-amino acid complex are partially distinguishable from one another. In some embodiments, gold or silver can be deposited onto the substrate as a form of surface enhancement for Raman spectroscopy. In one embodiment, surface enhancement for Raman spectroscopy are nanoparticles that interact with ClickP-amino acid complexes. In one embodiment, the interaction of the nanoparticles to ClickP-amino acid complexes are, but not limited to, covalent, hydrophilic or hydrophobic interaction.

As used herein, the terms "peptide", "polypeptide" or "protein" are used interchangeably herein and refer to two or more amino acids linked together by a peptide bond. The terms "peptide", "polypeptide" or "protein" includes peptides that are synthetic in origin or naturally occurring. As used herein "at least a portion of the peptide" refers to 2 or more amino acids of the peptide. Optionally, a portion of the peptide includes at least: 5, 10, 20, 30 or 50 amino acids, either consecutive or with gaps, of the complete amino acid sequence of the peptide, or the full amino acid sequence of the peptide.

The phrase "N-terminal amino acid" refers to an amino acid that has a free amine group and is only linked to one other amino acid by a peptide bond in the peptide. The phrase "N-terminal amino acid derivative" refers to a N-terminal amino acid residue that has been chemically modified, for example by an Edman reagent or other chemical in vitro or inside a cell via a natural post-translational modification (e.g. phosphorylation) mechanism, or a synthetic amino acid.

The phrase "C-terminal amino acid" refers to an amino acid that has a free carboxylic group and is only linked to one other amino acid by a peptide bond in the peptide. The phrase "C-terminal amino acid derivative" refers to a C-terminal amino acid residue that has been chemically modified, for example by a chemical reagent in vitro or inside a cell via a natural post-translational modification (e.g. phosphorylation) mechanism, or a synthetic amino acid.

The phrase "subgroup of ClickP-amino acid complexes" refers to a set of amino acids that are bound by the same ClickP-amino acid complex binder. In the broadest sense, the identity of the amino acid or subgroup is encoded in the binder. If the binder is not specific to one amino it may, for example, bind to 2 or 3 amino acids with some statistical regularity. This type of information is still relevant for protein identification since narrowing down the possibility of an amino acid is still relevant for database searches. Amino acid identity and binding variation is based on features like polarity, structure, functional groups and charge which can influence the specificity of the binder. Overall, the groups are based on the binder specificity and what they represent. A binder could bind two or more amino acids equally or with a varying degree of confidence, still providing sequence information.

As used herein, the binding of a binder to the ClickP-amino acid complex or subgroup of ClickP-amino acid complexes, refers to any covalent or non-covalent interaction between the binder and the ClickP-amino acid complex. In one embodiment, the binding is covalent. In one embodiment, the binding is non-covalent.

As used herein, "sequencing a peptide" refers to determining the amino acid sequence of a peptide. The term also refers to determining the sequence of a segment of a peptide or determining partial sequence information for a peptide. Partial sequencing of a peptide is still powerful and sufficient to discriminate protein identity when mapped back to available databases. For example, it is possible to uniquely identify 90% of the human proteome by sequencing six (6) consecutive terminal amino acids of a protein. In instances where a ClickP-amino acid complex binder that binds to a subgroup of ClickP-amino acid complexes, the binders may not provide exact identity of the terminal amino acid but instead the plausible subgroup identity. Plausible sequence identity information is still powerful and sufficient to discriminate protein identity when mapped back to available databases.

As used herein, "affixed" refer to a connection between a peptide and a substrate such that at least a portion of the peptide and the substrate are held in physical proximity. The terms "affixed" or "tethered" encompass both an indirect or direct connection and may be reversible or irreversible, for example the connection is optionally a covalent bond or a non-covalent bond.

In one embodiment, the substrate is a flat planar surface. In another embodiment, the substrate is 3-dimensional and exhibits surface features. In one embodiment the surface is a functionalized surface. In some embodiments, the substrate is a chemically derivatized glass slide or silica wafer.

As used herein "the cleaving the N-terminal amino acid or N-terminal amino acid derivative of the peptide" refers to a chemical reaction whereby the N-terminal amino acid or N-terminal amino acid derivative is removed from the peptide while the remainder of the peptide remains affixed to the substrate.

As used herein "the cleaving the C-terminal amino acid or C-terminal amino acid derivative of the peptide" refers to a chemical reaction whereby the C-terminal amino acid or C-terminal amino acid derivative is removed from the peptide while the remainder of the peptide remains affixed to the substrate.

As used herein the term "sample" includes any material that contains one or more polypeptides. Samples may be biological samples, such as biopsies, blood, plasma, organs, organelles, cell extracts, secretions, urine or mucous, tissue extracts and other biological samples of fluids both natural or synthetic in origin. The term sample also includes single cells. The sample may be derived from a cell, tissue, organism or individual that has been exposed to an analyte (such as a drug), or subject to an environmental condition, genetic perturbation, or combination thereof. The organisms or individuals may include, but are not limited to, mammals such as humans or small animals (rats and mice for example).

In one embodiment, the attachment points on the functionalized surface are spatially resolved. As used herein, the term "spatially resolved" refers to an arrangement of two or more polypeptides on a substrate wherein chemical or physical events occurring at one polypeptide can be distinguished from those occurring at the second polypeptide. For example, two polypeptides affixed on a substrate are spatially resolved if a signal from a detectable label bound to one of the polypeptides can be unambiguously assigned to one of the polypeptides at a specific location on the substrate.

In one embodiment, peptides to be sequenced are affixed to a substrate. In some embodiments, the substrate is made of a material such as glass, quartz, silica, plastics, metals, hydrogels, composites, or combinations thereof. In one embodiment, the substrate is a flat planar surface. In another embodiment, the substrate is 3-dimensional. In some embodiments, the substrate is a chemically derivatized glass slide or silica wafer.

In one embodiment, the substrate is made from material that does not substantially affect the sequencing reagents and assays described herein. In one embodiment, the substrate is resistant to the basic and acidic pH, chemicals and buffers used for Edman degradation. The substrate may also be covered with a coating. In some embodiments, the coating is resistant to the chemical reactions and conditions used in Edman degradation. In some embodiments, the coating provides attachment points for affixing polypeptides to the substrate, and/or repelling non-specific probe adsorption. In some embodiments, the coating provides attachment points for tethering the ClickP-peptide complex.

In some embodiments, the surface of the substrate is resistant to the non-specific adhering of polypeptides or debris, so as to minimize background signals when detecting the probes.

In one embodiment, the substrate made of a material that is optically transparent. As used herein, "optically transparent" refers to a material that allows light to pass through the material. In one embodiment, the substrate is minimally- or non-autofluorescent.

In one embodiment, the peptides are affixed to the substrate. In one embodiment, the peptides are affixed to the substrate such that the N-terminal or C-terminal end of the peptide is free to allow the binding of the ClickP compound. Accordingly, in some embodiments the peptide is affixed to the substrate through the N-terminal or C-terminal end of the peptide, the N-terminal amine or the C-terminal carboxylic acid group of the peptide. In some embodiments, the substrate contains one or more attachment points that permit a peptide to be affixed to the substrate.

In one embodiment, the peptides are affixed to the substrate such that the C-terminal end of the peptide is free to allow the binding of the ClickP compound. Accordingly, in some embodiments the peptide is affixed to the substrate through the N-terminal end of the peptide, the N-terminal amine group or a side chain function group of the peptide. In some embodiments, the substrate contains one or more attachment points that permit a polypeptide to be affixed to the substrate.

In some embodiments, the peptide is affixed through a covalent bond to the surface. For example, the surface of the substrate may contain a polyethylene glycol (PEG) or carbohydrate-based coating and the peptides are affixed to the surface via an N-hydroxysuccinimide (NHS) ester PEG linker.

A number of different chemistries for attaching linkers and peptides to a substrate are known in the art, for example by the use of specialized coatings that include aldehydesilane, epoxysilane or other controlled reactive moieties. In one embodiment, the substrate is glass coated with Silane or related reagent and the polypeptide is affixed to the substrate through a Schiff's base linkage through an exposed lysine residue.

In some embodiments the peptide is affixed non-covalently to the substrate. For example, in one embodiment the C-terminal end of the peptide is conjugated with biotin and the substrate comprises avidin or related molecules. In another embodiment, the C-terminal end of a peptide is conjugated to an antigen that binds to an antibody on the surface of the substrate. In another example, the N-terminal end of the peptide is conjugated with biotin and the substrate comprises avidin or related molecules. In another embodiment, the N-terminal end of a peptide is conjugated to an antigen that binds to an antibody on the surface of the substrate.

Additional coupling agents suitable for affixing a polypeptide to a substrate have been described in the art (See for example, Athena L. Guo and X. Y. Zhu. *The Critical Role of Surface Chemistry In Protein Microarrays* in Functional Protein Microarrays in Drug Discovery).

In one embodiment, there are provided ClickP-amino acid complex binders that preferentially bind to a specific ClickP-amino acid complex or a subgroup of ClickP-amino acid complexes. As used herein the phrase "preferentially binds to a specific ClickP-amino acid complex or a subgroup of ClickP-amino acid complexes" refers to a binder with a greater affinity for a specific or subgroup of ClickP-amino acid complexes compared to other specific or subgroup ClickP-amino acid complexes. A ClickP-amino acid complex binder preferentially binds a target ClickP-amino acid complex or a subgroup of ClickP amino acid complexes if there is a detectable relative increase in the binding of the binder to a specific or subgroup of ClickP-amino acid complexes.

In one embodiment, binders that preferentially bind to a specific ClickP-amino acid complex or a subgroup of ClickP-amino acid complexes are used to identify the N-terminal amino acid of a peptide. In one embodiment, binders that preferentially bind to a specific ClickP-amino acid complex or a subgroup of ClickP-amino acid complexes are used to sequence a peptide. In some embodiments, the binders are detectable with single molecule sensitivity.

In one embodiment, binders that preferentially bind to a specific ClickP-amino acid complex or a subgroup of ClickP-amino acid complexes are used to identify the C-terminal amino acid of a peptide. In one embodiment, binders that preferentially bind to a specific ClickP-amino acid complex or a subgroup of ClickP-amino acid complexes are used to sequence a peptide. In some embodiments, the binders are detectable with single molecule sensitivity.

In one embodiment, there are provided binders that selectively bind to a ClickP-amino acid complex or a ClickP-amino acid derivative complex. As used herein the phrase "selectively binds to a specific ClickP-amino acid complex" refers to a binder with a greater affinity for a specific ClickP-amino acid complex compared to other ClickP-amino acid complexes. A ClickP-amino acid complex binder selectively binds a target ClickP-amino acid complex if there is a detectable relative increase in the binding of the binder to a specific ClickP-amino acid complex.

In one embodiment, binders that selectively bind to a ClickP-amino acid complex or a ClickP-amino acid derivative complex are used to identify the N-terminal amino acid of a peptide. In one embodiment, binders that selectively bind to a ClickP-amino acid complex or a ClickP-amino acid derivative complex are used to sequence a polypeptide. In some embodiments, the binders are detectable with single molecule sensitivity.

In one embodiment, binders that selectively bind to a ClickP-amino acid complex or a ClickP-amino acid derivative complex are used to identify the C-terminal amino acid of a peptide. In one embodiment, binders that selectively bind to a ClickP-amino acid complex or a ClickP-amino acid derivative complex are used to sequence a peptide. In some embodiments, the binders are detectable with single molecule sensitivity.

The ClickP-amino acid binders that target and recognize a specific ClickP-amino acid complex or subgroup of ClickP-amino acid complexes can be a protein or peptide, a nucleic acid a chemical or combination. The binders may also include components containing non-canonical amino acid and synthetic nucleotides. In one embodiment, a protein binder can be, but not limited to, an antibody, or an enzyme such as peptidases, proteases, aminoacyl tRNA synthetase, peptides or transport proteins like lipocalin. In one embodiment, the antibody is a polyclonal antibody. In one embodiment, the antibody is a monoclonal antibody. In one embodiment, a nucleic acid binder can be, but not limited to, an aptamer DNA, RNA or a mix of synthetic nucleotides. Aptamers are DNA/RNA with binding properties. In one embodiment, a chemical binder can be, but not limited to amino acid reactive chemistries such as maleimide and NHS ester, heterofunctional chemicals with 2 or more different functional groups, or non-covalently binding supramolecular chemistries.

In one embodiment, the plurality of binders may include 20 binders that each selectively bind to one of the 20 natural proteinogenic amino acids. In another embodiment, the binders include 20 binders that each selectively bind to a derivative of one of the 20 natural proteinogenic amino acids complexed with ClickP. In one embodiment, the derivatives are phenylthiocarbamyl derivatives. In a further embodiment, the binders include binders that selectively bind to post-translationally-modified amino acids or their derivatives complexed with ClickP. In one embodiment, the binders include binders that selectively bind to synthetic amino acids or their derivatives complexed with ClickP.

Detecting the binders bound to the ClickP-amino acid complex can be accomplished by any detection method know by one of skill in the art.

In one embodiment, the binders include detectable labels. Detectable labels suitable for use with the present invention include, but are not limited to, labels that can be detected as a single molecule.

In one embodiment, the binders are detected by contacting the binders with a binder-specific antibody and the binder-specific antibody is then detected.

In some embodiments, the binders or labels are detected using magnetic or electrical impulses or signals.

In some embodiments, the labels on binders are oligonucleotides. Oligonucleotide labels are read out via any method known by one of skill in the art.

In one embodiment, the binders are detected by biological or synthetic nanopores via electrical impulses or signals.

In one embodiment, the labels are optically detectable, such as labels comprising a fluorescent moiety. Examples of optically detectable labels include, but are not limited to fluorescent dyes including polystyrene shells encompassing core dyes such as FluoSpheres™ Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. Additional detectable labels include color-coded nanoparticles, or quantum dots or FluoSpheres™. In one embodiment, the detectable label is resistant to photobleaching while producing lots of signal (such as photons) at a unique and easily detectable wavelength, with high signal-to-noise ratio.

One or more detectable labels can be conjugated to the binder reagents described herein using techniques known to a person of skill in the art. In one embodiment, a specific detectable label (or combination of labels) is conjugated to a corresponding binding reagent thereby allowing the identification of the binding reagent by means of detecting the label(s). For example, one or more detectable labels can be conjugated to the binding reagents described herein either directly or indirectly.

Binders bound to a ClickP-amino acid complex affixed to the substrate are detected, thereby identifying the terminal amino acid of the polypeptide or protein. In one embodiment, the binder is identified by detecting a detectable label (or combination of labels) conjugated to the binder. Methods suitable for detecting the binders described herein therefore depend on the nature of the detectable label(s) used in the method.

In one embodiment, the binders or labels are repeatedly detected at that location using a high resolution rastering laser/scanner across a pre-determined grid, unique position or path on a substrate. These methods are useful for the accurate and repeated detection of signals at the same coordinates during each sequencing cycle of the methods described herein. In some embodiments, the polypeptides are randomly affixed to the substrate and the detection of probes proceeds by repeatedly scanning the substrate to identify the co-ordinates and identities of probes bound to polypeptides affixed to the substrate.

In one embodiment, detecting the binders includes ultrasensitive detection systems that are able to repeatedly detect signals from precisely the same co-ordinates on a substrate, thereby assigning the detected sequence information to a unique polypeptide molecule affixed at that coordinate.

In one embodiment, the binders are detected using an optical detection system. Optical detection systems include a charge-coupled device (CCD), near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, total internal reflection fluorescence (TIRF) microscopy, super-resolution fluorescence microscopy, and single-molecule localization microscopy. In general, methods involve detection of laser-activated fluorescence using a microscope equipped with a camera, sometimes referred to as high-efficiency photon detection system. Suitable photon detection systems include, but are not limited to, photodiodes and intensified CCD cameras.

In one embodiment, examples of techniques suitable for single molecule detection of fluorescent probes include confocal laser (scanning) microscopy, wide-field microscopy, near-field microscopy, fluorescence lifetime imaging microscopy, fluorescence correlation spectroscopy, fluorescence intensity distribution analysis, measuring brightness changes induced by quenching/dequenching of fluorescence, or fluorescence energy transfer.

In one embodiment, the ClickP complex is cleaved from the peptide. In one embodiment, cleaving exposes the terminus of an adjacent amino acid on the peptide, whereby the adjacent amino acid is available for reaction with a ClickP compound. Optionally, the peptide is sequentially cleaved until the last amino acid in the peptide.

In some embodiments, the C-terminal amino acid is covalently affixed to the substrate and is not cleaved from the substrate. In one embodiment, cleaving exposes the N-terminus of an adjacent amino acid on the peptide, whereby the adjacent amino acid is available for reaction with a ClickP compound. Optionally, the peptide is sequentially cleaved until the last amino acid in the peptide (C-terminal amino acid).

In some embodiments, the N-terminal amino acid is covalently affixed to the substrate and is not cleaved from the substrate. In one embodiment, cleaving exposes the C-terminus of an adjacent amino acid on the peptide, whereby the adjacent amino acid is available for reaction with a ClickP compound. Optionally, the peptide is sequentially cleaved until the last amino acid in the peptide (N-terminal amino acid).

In one embodiment, sequential terminal degradation is used to cleave the N-terminal amino acid of the peptide. In one embodiment, sequential terminal degradation is used to cleave the C-terminal amino acid of the peptide. Degradation generally comprises two steps, a coupling step and a cleaving step. These steps may be iteratively repeated, each time removing the exposed terminal amino acid residue of a peptide.

In one embodiment terminal degradation proceeds by way of contacting the peptide with a suitable reagent such as PITC or a PITC analogue at an elevated pH to form a N-terminal phenylthiocarbamyl derivative. Reducing the pH, such by the addition of trifluoroacetic acid results in the cleaving the N-terminal amino acid phenylthiocarbamyl derivative from the polypeptide to form a free anilinothiozolinone (ATZ) derivative. This ATZ derivative may be detected. In one embodiment, ATZ derivatives can be converted to phenylthiohydantoin (PTH) derivatives by exposure to acid. This PTH derivative may be detected. In one embodiment, ATZ derivatives and PTH derivatives can be converted to phenylthiocarbamyl (PTC) derivatives by exposure to a reducing agent. This PTC derivative may be detected. In one embodiment the pH of the substrate's environment in controlled in order to control the reactions governing the coupling and cleaving steps.

In embodiments, terminal degradation proceeds by way of contacting the peptide with a suitable reagent such as ammonium thiocyanate after activation with acetic anhydride to form a C-terminal peptidylthiohydantion derivative. Reducing the pH, with a Lewis Acid results in the cleaving the C-terminal amino acid peptidylthiohydantion derivative by resulting in an alkylated thiohydantoin (ATH) leaving group from the polypeptide to form a free thiohydantion derivative. This ATH derivative may be detected. In one embodiment, ATH derivatives can be converted to thiohydantoin derivatives by exposure to acid. This thiohydantoin derivative may be detected. In one embodiment, the pH of the substrate's environment in controlled in order to control the reactions governing the coupling and cleaving steps.

In one embodiment, the steps of contacting the peptide with a ClickP compound, wherein the ClickP compound binds to an N-terminal amino acid or N-terminal amino acid derivative to form a ClickP-peptide complex, tethering the ClickP-peptide complex to a substrate; cleaving the ClickP-peptide complex from the peptide resulting in a ClickP-amino acid complex; detecting and/or identifying the amino acid of the ClickP-amino acid complex, and releasing the ClickP-amino acid complex from the substrate are repeated in order to sequence the peptide. Optionally, the steps are repeated at least 2, 5, 10, 20, 30, 50, or greater than 50 times in order to sequence part of or the complete peptide. Optionally at least: 2, 5, 10, 20 30 or 50 contiguous or discontiguous amino acid residues of the amino acid sequence of the peptide or the full amino acid sequence of the peptide are determined.

In one embodiment, the steps of contacting the peptide with a ClickP compound, wherein the ClickP compound binds to an C-terminal amino acid or C-terminal amino acid derivative to form a ClickP-peptide complex, tethering the ClickP-peptide complex to a substrate; cleaving the ClickP-peptide complex from the peptide resulting in a ClickP-amino acid complex; detecting and/or identifying the amino acid of the ClickP-amino acid complex, and releasing the ClickP-amino acid complex from the substrate are repeated in order to sequence the peptide. Optionally, the steps are repeated at least 2, 5, 10, 20, 30, 50, or greater than 50 times in order to sequence part of or the complete peptide. Optionally at least: 2, 5, 10, 20 30 or 50 contiguous or discontiguous amino acid residues of the amino acid sequence of the peptide or the full amino acid sequence of the peptide are determined.

In one embodiment, the method further includes washing or rinsing the substrate before or after any one of the steps of affixing the substrate, contacting the peptide with a ClickP compound, tethering the ClickP-peptide complex to a substrate; cleaving the ClickP-peptide complex from the peptide; detecting and/or identifying the amino acid of the ClickP-amino acid complex; and releasing the ClickP-amino acid complex from the substrate. Washing or rinsing the substrate removes waste products such as cleaved N-terminal amino acids or C-terminal amino acids, debris or previously unused reagents from the substrate that could interfere with the next step in the sequencing assay.

The methods described herein allow for the sequencing of very large number of peptide molecules on a single substrate or on a series of substrates. Accordingly, one aspect of the invention provides for simultaneously sequencing a plurality of affixed peptides initially present in a sample. In one embodiment, the sample comprises a cell extract or tissue extract. In some embodiments, the methods described herein may be used to analyze the peptides contained in a single cell. In a further embodiment, the sample may comprise a biological fluid such as blood, urine or mucous. Soil, water or other environmental samples bearing mixed organism communities are also suitable for analysis.

In one embodiment, the sample comprises a mixture of synthetically synthesized peptides.

In one embodiment of the description, the method includes comparing the sequence of each peptide to a reference protein sequence database. In some embodiments, small fragments comprising 10-20 or fewer sequenced amino acid residues may be useful for detecting the identity of a peptide in a sample.

In one embodiment, the method includes de novo sequencing of peptides in order to generate sequence information about the peptide. In another embodiment, the method includes determining a partial sequence or an amino acid pattern and then matching the partial sequence or amino acid patterns with reference sequences or patterns contained in a sequence database.

In one embodiment, the method includes using the sequence data generated by the method as a molecular fingerprint or in other bioinformatic procedures to identify characteristics of the sample, such as cell type, tissue type or organismal identity.

In addition, as each peptide affixed to the substrate is optionally monitored individually, the method is useful for the quantitative analysis of protein expression. For example, in some embodiments, the method comprises comparing the sequences of each peptide, grouping similar peptide sequences and counting the number of instances of each similar peptide sequence. The methods described herein are therefore useful for molecular counting or for quantifying the number of peptides in a sample or specific kinds of peptides in a sample.

In a further embodiment, cross-linked peptides are sequenced using the methods described herein. For example, a cross-linked protein may be affixed to a substrate and two or more N-terminal amino acids are then bound and sequenced. The overlapping signals that are detected correspond to binders each binding the two or more terminal amino acids at that location. In one embodiment, it is possible to deduce or deconvolute the two multiplexed/mixed sequences via a computational algorithm and DB search.

In a further embodiment, the methods described herein are useful for the analysis and sequencing of phosphopeptides. For example, polypeptides in a sample comprising phosphopeptides are affixed to a substrate via metal-chelate chemistry. The phosphopolypeptides are then sequenced according to the methods described herein, thereby providing sequence and quantitative information on the phosphoproteome.

Additional multiplexed single molecule read-out and fluorescent amplification schemes can involve conjugating the binders with DNA barcodes and amplification with hybridized chain reaction (HCR). HCR involves triggered self-assembly of DNA nanostructures containing fluorophores and provides multiplexed, isothermal, enzyme-free, molecular signal amplification with high signal-to-background. HCR and branched DNA amplification can allow a large number of fluorophores to be targeted with single-barcode precision.

EXAMPLES

Example 1 Characterize and Validate ClickP Function

The ability to conjugate and cleave N-terminal amino acids was determined using the ClickP compound as shown in FIG. 1. The clickable alkyne group on ClickP was also be tested to ensure ClickP can link with azide conjugates.

ClickP cleavage involved conjugating the PITC group to a peptide of known molecular weight and measuring the molecular weight before and after cleavage using mass spectrometry. The expected reduction in molecular weight by loss of one amino acid would signify a successful cleavage. Mass spectrometry was performed on the peptide only without ClickP, peptide with ClickP conjugated to the N-terminal amino acid, and the cleaved peptide after ClickP removes the N-terminal amino acid. Based on the mass spectrometry results, efficiencies of the conjugation and cleavage to the N-terminal amino acid of two candidate ClickP compounds when compared to PITC is shown in FIG. 3.

Figure 3A:
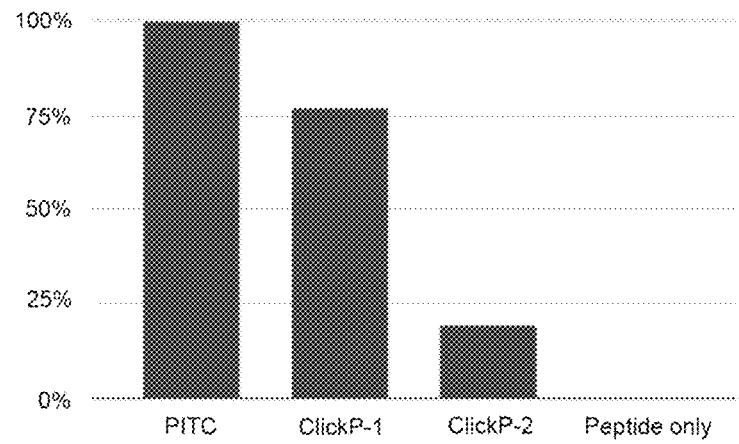
FIG. 3A through FIG. 3C depict the efficiency of ClickP candidates to conjugate and cleave the N-terminal primary amine when compared to PITC.
Figure 3B:
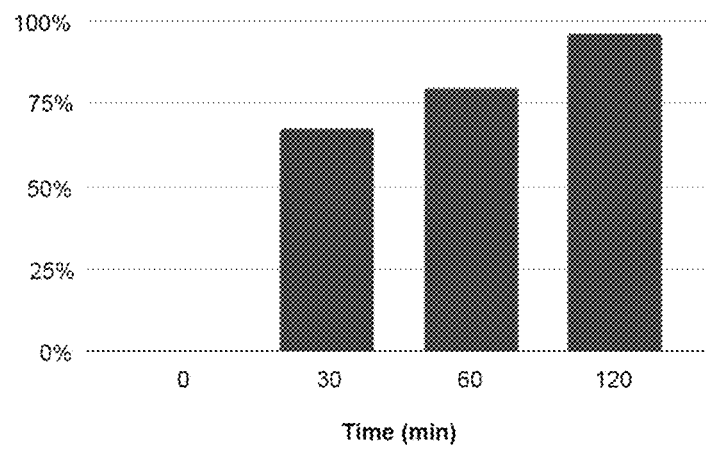
Figure 3C:
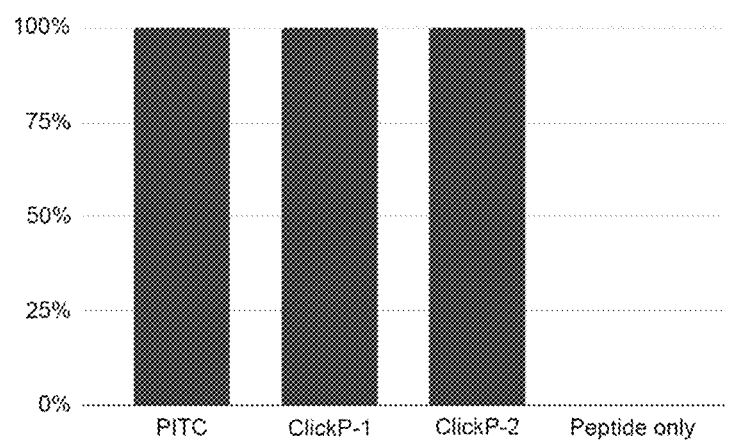

FIG. 3A compares the N-terminal conjugation efficiency of PITC, ClickP1, ClickP2 and only peptide. FIG. 3B demonstrates that ClickP1 can achieve PITC N-terminal conjugation efficiency at longer reaction time periods. FIG. 3C compares the N-terminal cleavage efficiency of PITC, ClickP1, ClickP2 and only peptide. Data was collected with LCMS to determine amount reactant and the amount of product. Based on these results, ClickP candidates are capable of conjugating to the N-terminal end of the peptide and cleaving the N-terminal amino acid to efficiencies comparable to PITC.

Figure 4:
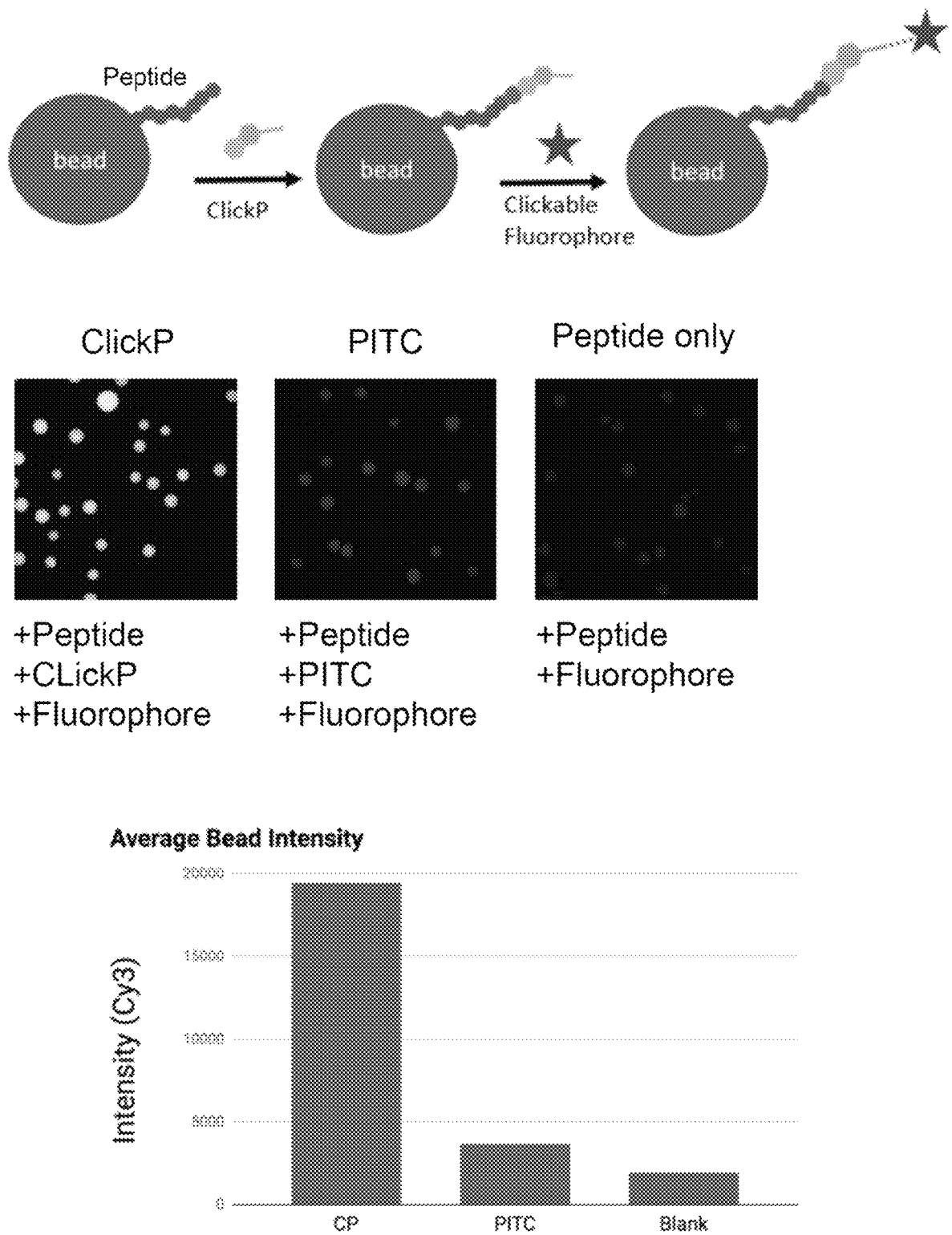
FIG. 4 demonstrates the activity of the tethering group of the ClickP compound.

The functionality of the alkyne group and its ability to conjugate to azide-substrates was determined. To demonstrate this, functionalized beads were either coated without peptide (control) or with immobilized peptides. Following coating, beads were incubated with ClickP to facilitate conjugation to the N-terminal amino acid of the peptides. Next, the clickable group of ClickP was reacted to an azide connected to a fluorophore tetramethylrhodamine (TMR) followed by a washing step. Since the reactive azide-fluorophore should only react to the alkyne group of ClickP, ClickP conjugated to the peptide containing beads should be higher in fluorescent intensity when the azide-fluorophore is introduced. The increase in fluorescence when compared to the control would be indicative of a functional azide-alkyne click chemistry on the ClickP reagent. The results are shown in FIG. 4.

The tethering functional group of ClickP will also be tested to ensure that it forms a bond with functionalized surfaces for immobilizing ClickP, whether it is stable under Edman conditions of high heat and low pH, and if the reducing agent cleaves the bond. For example, the modular thiol-azide linker will be tested to ensure that it forms a disulfide bond with thiol-functionalized surfaces for conditionally immobilizing ClickP. This validation will involve using the linker to form disulfide bonds on thiol-functionalized beads and using the azide group on the linker to conjugate to an alkyne-fluorophore conjugate. Adding the reducing agent TCEP is expected to cleave the disulfide bond and release the linker conjugated to the fluorophore, thus reducing the fluorescent intensity. Controls would test whether disulfide bonds under Edman conditions would cleave and release the fluorophore and also whether the fluorophore itself is stable when exposed to TCEP and Edman conditions. The fluorophore would be directly conjugated to beads and expected to maintain the same fluorescent intensity when under high heat, low pH and exposed to the reducing agent TCEP.

Example 2: Reagent for Amino Acid Recognition ("Binder" of the ClickP-Amino Acid Complex)

Single-molecule peptide or protein sequence inherently involves elucidating the amino acid composition and order. All amino acids are organic small molecule compounds that contain amine (—NH2) and carboxyl (—COOH) functional groups, differentiated by their respective side chain (R group). The ability to identify all 20 amino acid requires a set of reagents or methods capable of discriminating their molecular structure with high specificity.

Figure 5A:
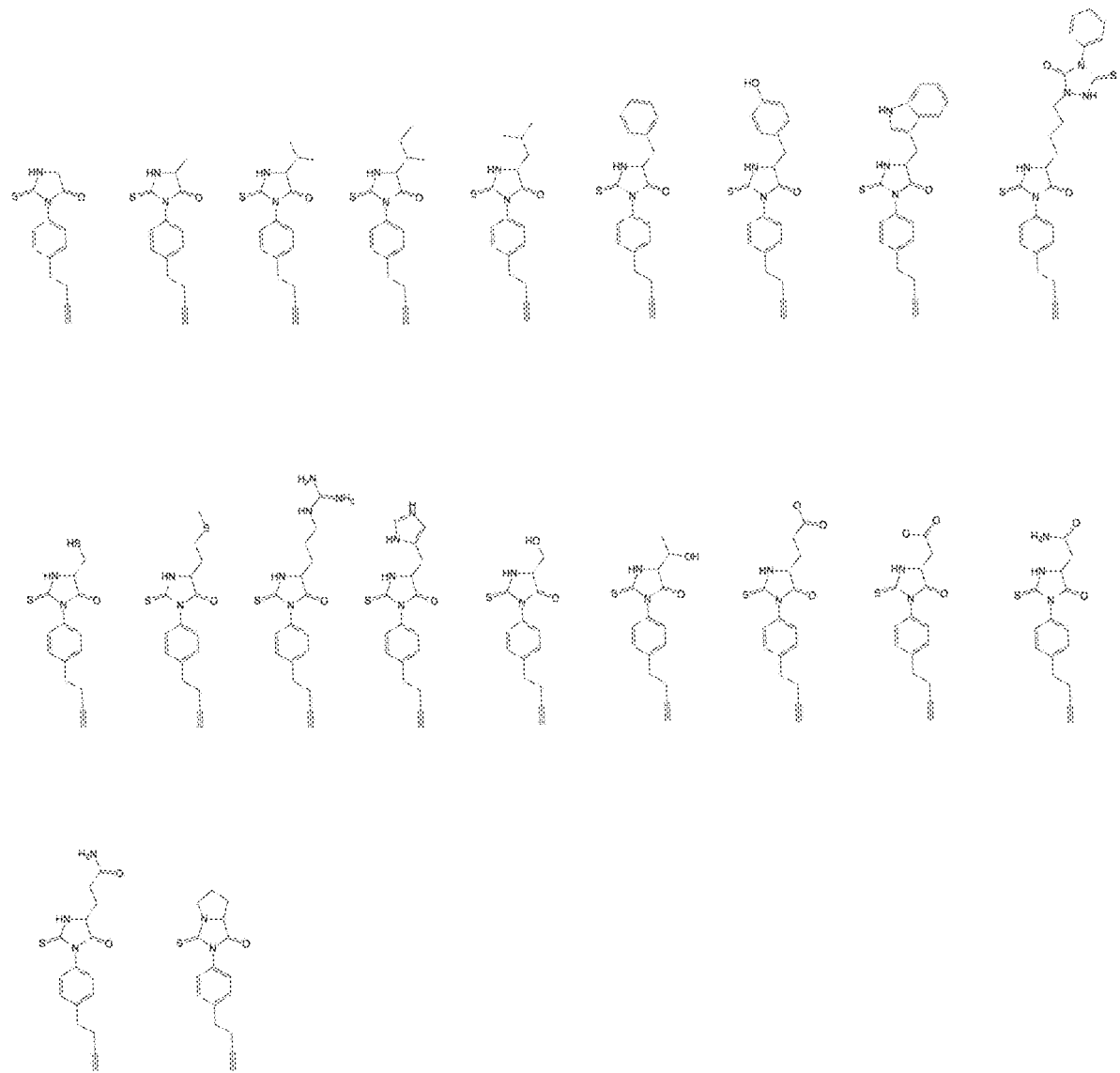
FIG. 5A and FIG. 5B depict examples of a ClickP compound bound to all 20 natural amino acids.
Figure 5B:
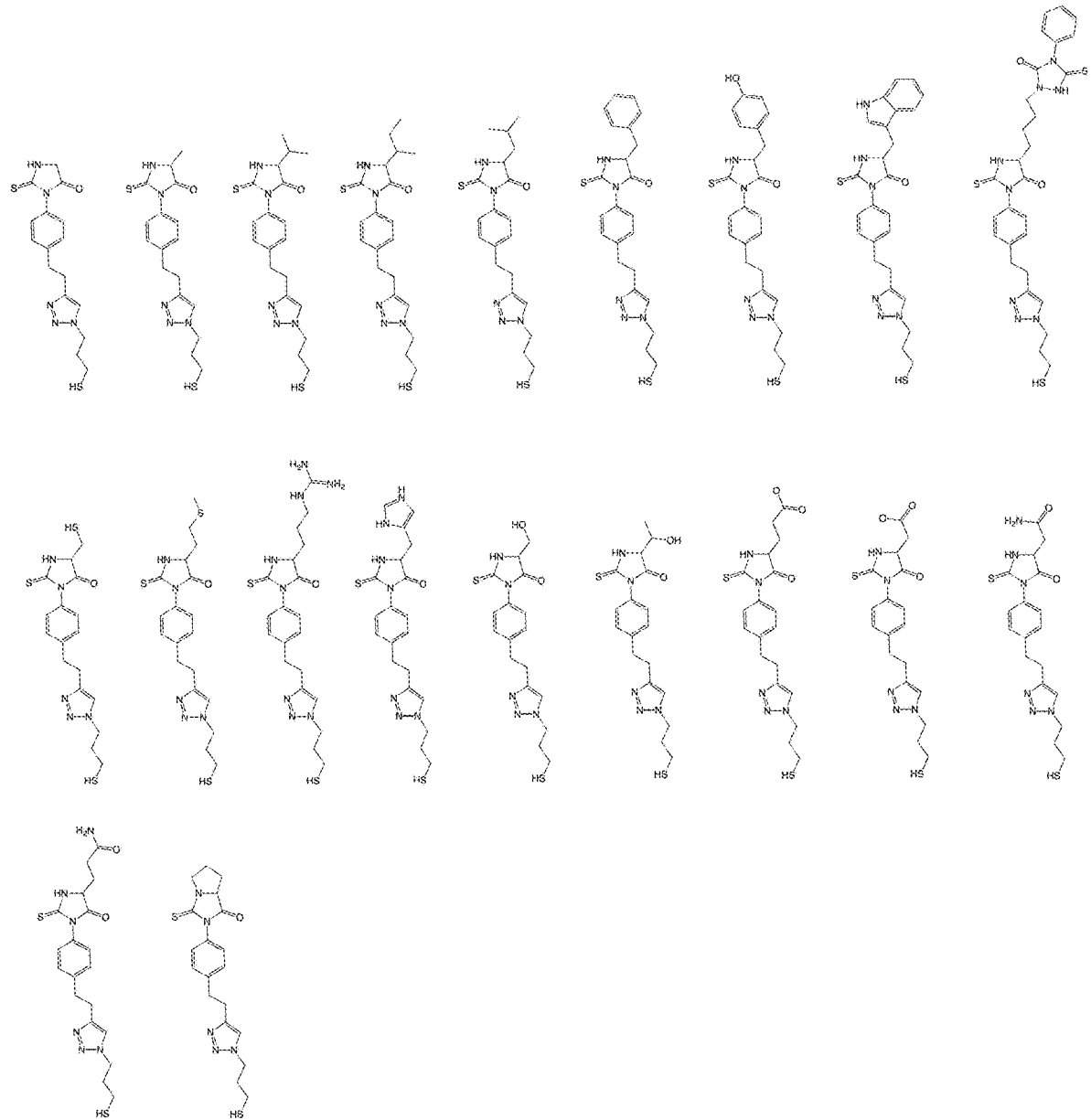
Figure 6B:
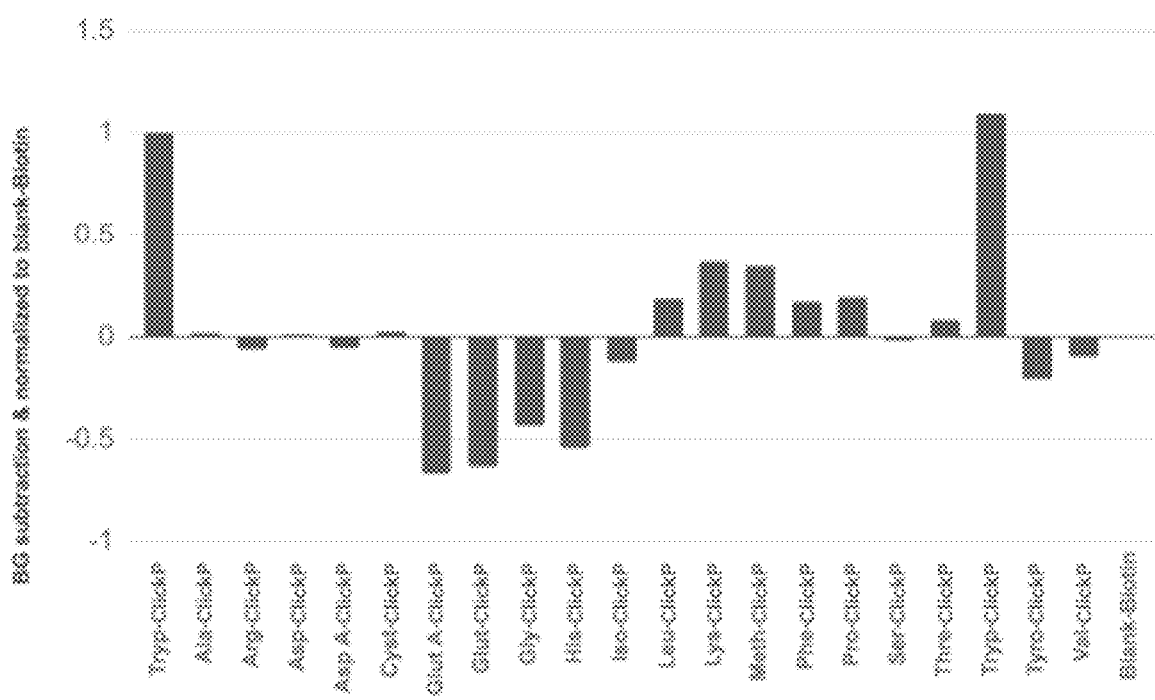
Figure 7:
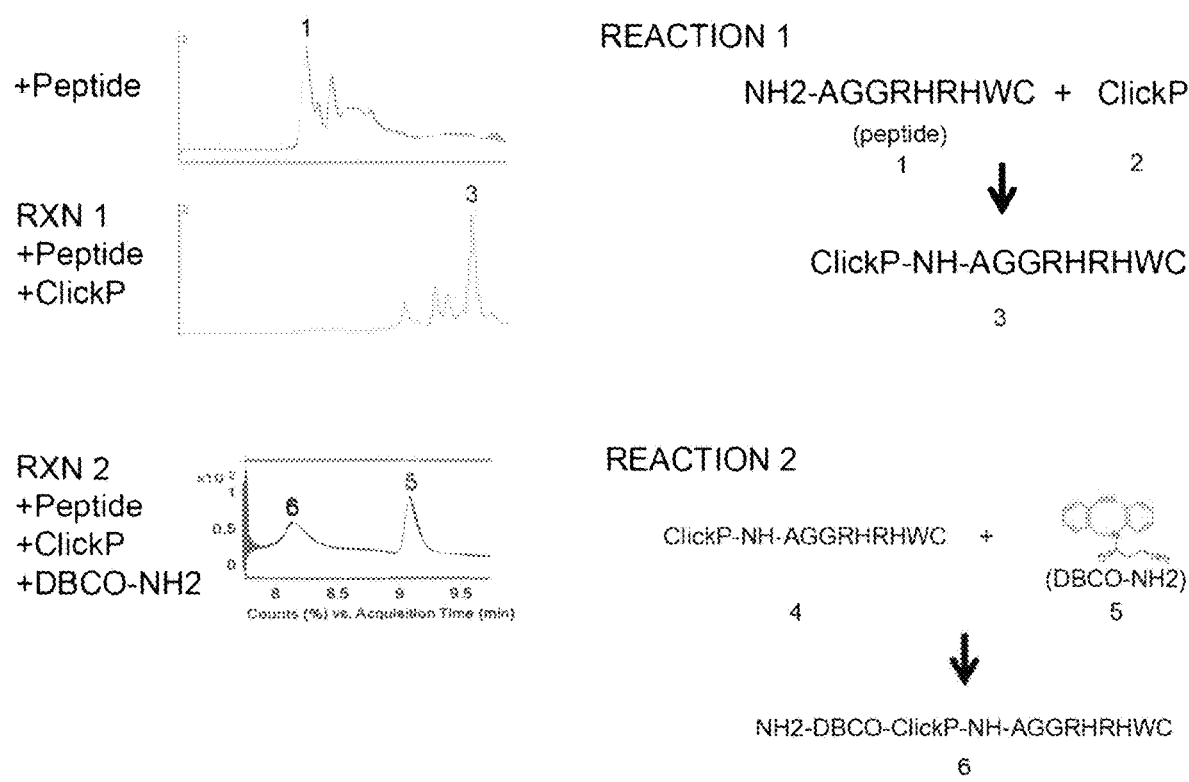
FIG. 7 depicts the mass spectrometry results of ClickP conjugation and cleavage of N-terminal amino acid.
Figure 7:
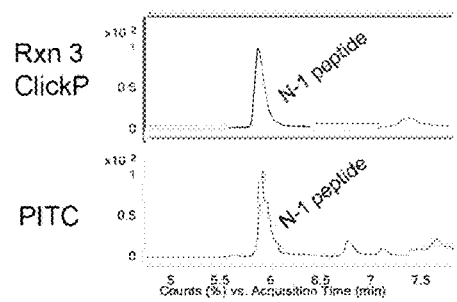
Figure 7:
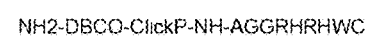
Figure 7:
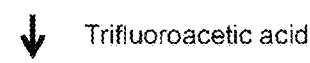
Figure 7:
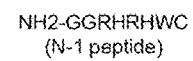

ClickP-based amino acid isolation solves the "local environment" problem, which is define as the interference of a binder's ability to bind to a specific terminal amino acid due to the variability of adjacent amino acids. FIG. 6A demonstrates that the binding efficiency of an antibody targeting tryptophan at the N-terminal amino acid is perturbed by adjacent amino acids. Binding amount was quantified by biolayer interferometry. By removing the local environment problem with ClickP, binders are intended to target ClickP-amino acids instead of the terminal amino acid. FIG. 5 shows a portion of a possible ClickP compound bound to all 20 amino acids. In FIG. 6B, a tryptophan antibody can discriminate ClickP-tryptophan from other amino acids. This indicates that binders are capable of targeting specific ClickP amino acids.

To obtain more selective binders, portions of the ClickP-amino acid complexes can be used as small molecules for the development of antibodies with high affinity and specificity.

In one method, the ClickP-amino acid complexes can be injected into rabbits to elicit an immune response against the compounds and, thereby, the production of antibodies to bind the ClickP-amino acid complexes.

Downstream, the monoclonal antibodies generated via rabbit hybridoma technology will be tested for affinity, specificity and cross-reactivity. The antibodies secreted by the different clones will be assayed for cross-reactivity using enzyme-linked immunosorbent assay (ELISA) 29 and affinity will be measured using the label-free method BioLayer Interferometry (BLI) 30 for measuring the kinetics of protein-ligand interactions.

If antibodies do not display robust affinity or specificity towards ClickP bound amino acids, directed evolution approaches can be used for improving antibody affinity and specificity. Antibody binders can be engineered to target each amino acid isolated with ClickP using yeast display, a protein engineering technique that uses the expression of recombinant proteins incorporated into the cell wall of yeast to screen and evolve high affinity ligands. Yeast display has been used to successfully engineer antibodies that target small molecules with high affinity. The clones generated from the rabbit hybridoma can be used to construct an antibody library in yeast. The library will already have a bias towards the ClickP target so directed evolution via mutagenesis can introduce novel antibody variants with improved characteristics. Yeast Display is also capable of negative selection which helps remove antibodies that cross-react with other targets. Negative selection would involve incubating yeast expressing the antibody library with magnetic beads conjugated to non-target antigens and pulling them out of solution. For example, when targeting ClickP bound to one particular amino acid, the other 19 amino acids can be negatively selected against to improve the odds of a highly specific binder.

In parallel, other binders such as enzymes or nucleic acid aptamers can be explored in case hybridoma technology does not generate any antibodies that target ClickP-bound amino acids. There exists 20 aminoacyl-tRNA synthetase enzymes that recognize their respective amino acids. Aminoacyl-tRNA synthetases or any other amino acid binding protein in nature can be used as scaffold proteins on yeast display and undergo directed evolution to select for specificity and affinity towards respective ClickP-bound amino acids. DNA/RNA aptamers are single-stranded oligonucleotides capable of binding various molecules with high specificity and affinity. It is established that RNA is able to form specific binding sites for free amino acids and that RNA aptamers have been evolved to change its binding specificity through repeated rounds of in vitro selection-amplification techniques of random RNA pools.

Antibody binders can simply have conjugated fluorophores or secondary antibodies conjugated to fluorophores that bind to the primary antibody, amplifying fluorescent intensity.

After binders are generated for targeting ClickP-bound amino acids, the sequencing scheme and imaging platform will be implemented on peptides, proteins and cell lysates.

Example 3: Imaging and Scaling to Proteome

Amino acids can be identified by integrating all components of ClickP isolation of N-terminal amino acids, labeling with ClickP-amino acid specific binders, imaging, and release of ClickP for subsequent cycles of amino acid identification. Sufficient cycles of amino acid identification will provide protein sequencing information.

Peptides will first be immobilized by the C-terminus with carboxy crosslinking chemistry. Next, ClickP binds to the N-terminal amino acid of the peptide and tethers to a functionalized substrate with the addition of a removable group. Following N-terminal cleavage, the isolated ClickP-bound amino acid is labeled with binders, imaged and removed.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for generating a ClickP-peptide complex, comprising:
   (a) providing a portion of a ClickP compound, wherein the portion of the ClickP compound comprises a terminal amino acid reactive group capable of conjugating to a terminal amino acid or a terminal amino acid derivative of a peptide, a tetherable group, and a spacer comprising a hydrocarbon chain, wherein the spacer is disposed between the terminal amino acid reactive group and the tetherable group;
   (b) attaching a releasable group comprising an oligonucleotide to the tetherable group; and
   (c) reacting the terminal amino acid reactive group with the terminal amino acid or the terminal amino acid derivative of the peptide, thereby generating the ClickP-peptide complex.

2. The method of claim 1, further comprising, (d) cleaving the terminal amino acid or the terminal amino acid derivative from the peptide, thereby generating a ClickP compound-terminal amino acid complex.

3. The method of claim 2, wherein (d) is performed by addition of an acid.

4. The method of claim 3, wherein the acid is a Lewis acid.

5. The method of claim 2, further comprising repeating (a)-(d).

6. The method of claim 2, wherein, subsequent to (d), the peptide and/or the ClickP compound-terminal amino acid complex are immobilized to a substrate.

7. The method of claim 2, further comprising (e) detecting the ClickP compound-terminal amino acid complex.

8. The method of claim 7, wherein detecting the ClickP compound-terminal amino acid complex comprises contacting the ClickP compound-terminal amino acid complex with one or more ClickP compound-amino acid complex binders.

9. The method of claim 8, wherein the one or more ClickP compound-amino acid complex binders comprise:
   (i) one or more binders that bind to a derivative of one of 20 natural proteinogenic amino acids complexed with the ClickP compound;
   (ii) one or more binders that bind to a subgroup of derivatives of the 20 natural proteinogenic amino acids complexed with the ClickP compound;
   (iii) one or more binders that bind to a derivative of a post-translationally modified amino acid complexed with the ClickP compound;
   (iv) one or more binders that bind to a subgroup of derivatives of post-translationally modified amino acids complexed with the ClickP compound; or
   (v) a combination of two or more of (i)-(iv).

10. The method of claim 8, wherein the one or more ClickP compound-amino acid complex binders comprises a detectable label.

11. The method of claim 1, wherein the terminal amino acid reactive group comprises one or more of an isothiocyanate, phenyl isothiocyanate (PITC), an isocyanate, acyl azide, N-hydroxysuccinimide ester (NHS ester), sulfonyl chloride, an aldehyde, a glyoxal, an epoxide, an oxirane, a carbonate, an aryl halide, an imidoester, a carbodiimide, an anhydride, a fluorophenyl ester, tetrabutylammonium isothiocyanate, diphenylphosphoryl isothiocyanate, acetyl chloride, cyanogen bromide, sodium thiocyanate, ammonium thiocyanate, and a carboxypeptidase.

12. The method of claim 1, wherein the tetherable group comprises one or more of an isothiocyanate, tetrabutylammonium isothiocyanate, diphenylphosphoryl isothiocyanate, azide, an alkyne, Dibenzocyclooctyne (DBCO), maleimide, succinimide, a thiol-thiol disulfide bond, Tetrazine, TCO, Vinyl, methylcyclopropene, a primary amine, a carboxylic acid, an alkyne, an acryloyl, an allyl, and an aldehyde.

13. The method of claim 1, wherein the terminal amino acid or the terminal amino acid derivative is an N-terminal amino acid or an N-terminal amino acid derivative.

14. The method of claim 1, wherein the terminal amino acid or the terminal amino acid derivative is a C-terminal amino acid or a C-terminal amino acid derivative.

15. The method of claim 1, wherein the peptide is affixed to a substrate.

16. The method of claim 15, wherein the peptide is affixed to the substrate via an N-hydroxysuccinimide (NHS) ester PEG linker.

17. The method of claim 1, wherein the spacer "further" comprises one or more of a polyethylene glycol (PEG) chain, aminohexanoic acid (Ahx), 12-amino-dodecanoic acid, O2Oc, O1Pen-O1Pen, Ttds, Beta-Alanine, amino acid, peptide, peptide bond, and nucleic acid.
18. The method of claim 1, wherein the tetherable group is a click chemistry moiety.
19. The method of claim 1, wherein the portion of the ClickP compound is Formula II:
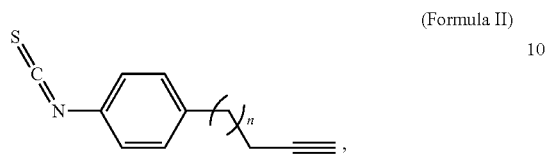
(Formula II)
wherein n is any number from 0 to 500.
20. The method of claim 1, wherein the peptide is derived from a biological sample.
* * * * *

UNITED STATES PATENT AND TRADEMARK OFFICE
CERTIFICATE OF CORRECTION

PATENT NO. : 12,379,380 B2
APPLICATION NO. : 18/615276
DATED : August 5, 2025
INVENTOR(S) : Daniel Masao Estandian et al.

Page 1 of 1

It is certified that error appears in the above-identified patent and that said Letters Patent is hereby corrected as shown below:

In the Claims

In Claim 17, Line 65, please replace ""further"" with --further--.

Signed and Sealed this
Ninth Day of September, 2025

Coke Morgan Stewart
*Acting Director of the United States Patent and Trademark Office*